(12) United States Patent
Wang et al.

(10) Patent No.: US 11,837,015 B2
(45) Date of Patent: Dec. 5, 2023

(54) IMAGING APPARATUS AND IMAGING METHOD

(71) Applicant: SONY GROUP CORPORATION, Tokyo (JP)

(72) Inventors: Qihong Wang, Tokyo (JP); Masatomo Kurata, Tokyo (JP); Hiroyuki Shigei, Tokyo (JP); Naoko Kobayashi, Tokyo (JP); Toru Amano, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 64 days.

(21) Appl. No.: 17/612,467

(22) PCT Filed: May 18, 2020

(86) PCT No.: PCT/JP2020/019695
§ 371 (c)(1),
(2) Date: Nov. 18, 2021

(87) PCT Pub. No.: WO2020/241364
PCT Pub. Date: Dec. 3, 2020

(65) Prior Publication Data
US 2022/0222966 A1    Jul. 14, 2022

(30) Foreign Application Priority Data
May 28, 2019 (JP) .................................. 2019-099714

(51) Int. Cl.
*G06V 40/13* (2022.01)
*G06V 40/12* (2022.01)

(52) U.S. Cl.
CPC ...... *G06V 40/1394* (2022.01); *G06V 40/1318* (2022.01); *G06V 40/1365* (2022.01)

(58) Field of Classification Search
CPC ........... G06V 40/1394; G06V 40/1318; G06V 40/1365; G06V 40/1335
See application file for complete search history.

(56) References Cited

U.S. PATENT DOCUMENTS

| | | | |
|---|---|---|---|
| 10,216,975 B1 | 2/2019 | He et al. | |
| 2008/0159599 A1 | 7/2008 | Kajihara et al. | |

(Continued)

FOREIGN PATENT DOCUMENTS

| | | |
|---|---|---|
| CN | 101661555 A | 3/2010 |
| CN | 103370727 A | 10/2013 |

(Continued)

OTHER PUBLICATIONS

International Search Report and Written Opinion of PCT Application No. PCT/JP2020/019695, dated Aug. 18, 2020, 12 pages of ISRWO.

(Continued)

*Primary Examiner* — Stephen G Sherman
(74) *Attorney, Agent, or Firm* — CHIP LAW GROUP

(57) ABSTRACT

Provided is an imaging apparatus that includes an irradiation unit that irradiates a subject with light, an imaging unit that images the subject a plurality of times, a control unit that controls the imaging unit and the irradiation unit, and a combination unit that combines a plurality of imaged images obtained by the imaging unit. The imaging unit has a plurality of imaging elements disposed in a matrix when viewed from the side of the subject. The irradiation unit has a plurality of light emitting elements provided so as to correspond to the plurality of imaging elements. The control unit controls the irradiation unit to turn on the plurality of light emitting elements different for each imaging among the plurality of light emitting elements, and controls the imaging unit to drive the plurality of imaging elements corresponding (Continued)

to the plurality of light emitting elements that are not turned on.

20 Claims, 34 Drawing Sheets

(56) References Cited

U.S. PATENT DOCUMENTS

| | | | |
|---|---|---|---|
| 2010/0046807 | A1 | 2/2010 | Sato |
| 2011/0013074 | A1* | 1/2011 | Ichimura ............ H01L 27/14627 |
| | | | 382/129 |
| 2013/0329031 | A1 | 12/2013 | Miura et al. |
| 2016/0092717 | A1 | 3/2016 | Ling |
| 2017/0337412 | A1 | 11/2017 | Bhat et al. |
| 2017/0364763 | A1* | 12/2017 | Jin ........................ G06F 3/0416 |
| 2018/0060641 | A1* | 3/2018 | Kim ................... G06V 40/1324 |
| 2019/0013368 | A1 | 1/2019 | Chung et al. |

FOREIGN PATENT DOCUMENTS

| | | | |
|---|---|---|---|
| CN | 108598117 | A | 9/2018 |
| CN | 108960068 | A * 12/2018 | ............ G06K 9/0004 |
| CN | 109216421 | A | 1/2019 |
| CN | 109414225 | A | 3/2019 |
| EP | 2704093 | A1 | 3/2014 |
| EP | 3425670 | A1 | 1/2019 |
| JP | 2008-165742 | A | 7/2008 |
| JP | 2008-210407 | A | 9/2008 |
| JP | 2010-049664 | A | 3/2010 |
| JP | 2017-196319 | A | 11/2017 |
| JP | 2019-033071 | A | 2/2019 |
| JP | 2019-521734 | A | 8/2019 |
| KR | 10-2019-0004678 | A | 1/2019 |
| KR | 10-2019-0025841 | A | 3/2019 |
| WO | 2012/143977 | A1 | 10/2012 |
| WO | 2017/205298 | A1 | 11/2017 |

OTHER PUBLICATIONS

Extended European Search Report of EP Application No. 20813009. 6, dated Jun. 27, 2022, 08 pages.

* cited by examiner

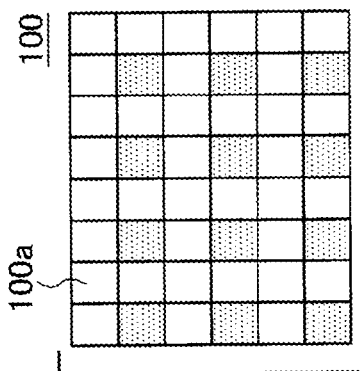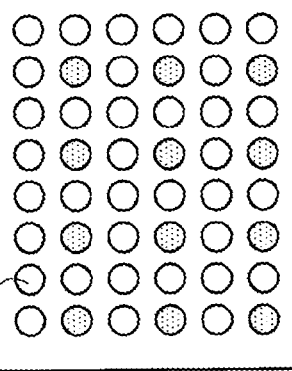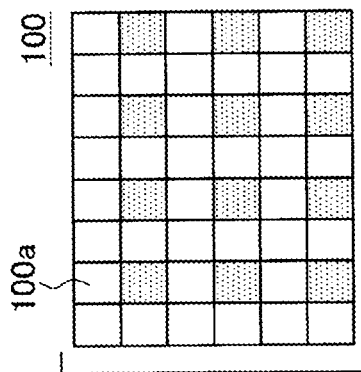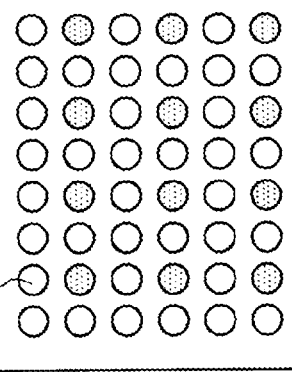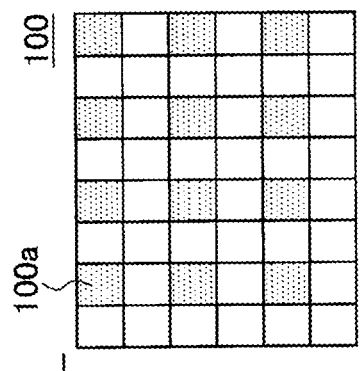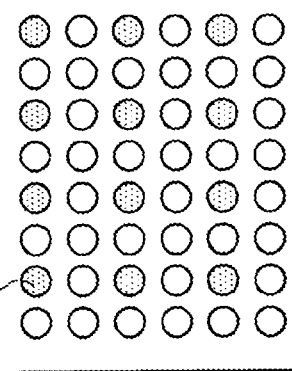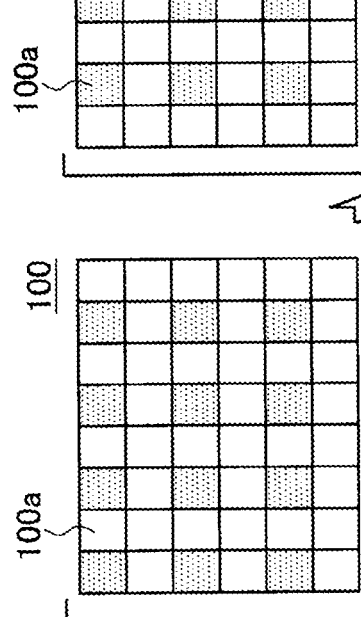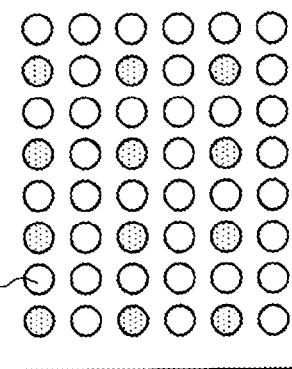
FIG. 29A  FIG. 29B  FIG. 29C  FIG. 29D

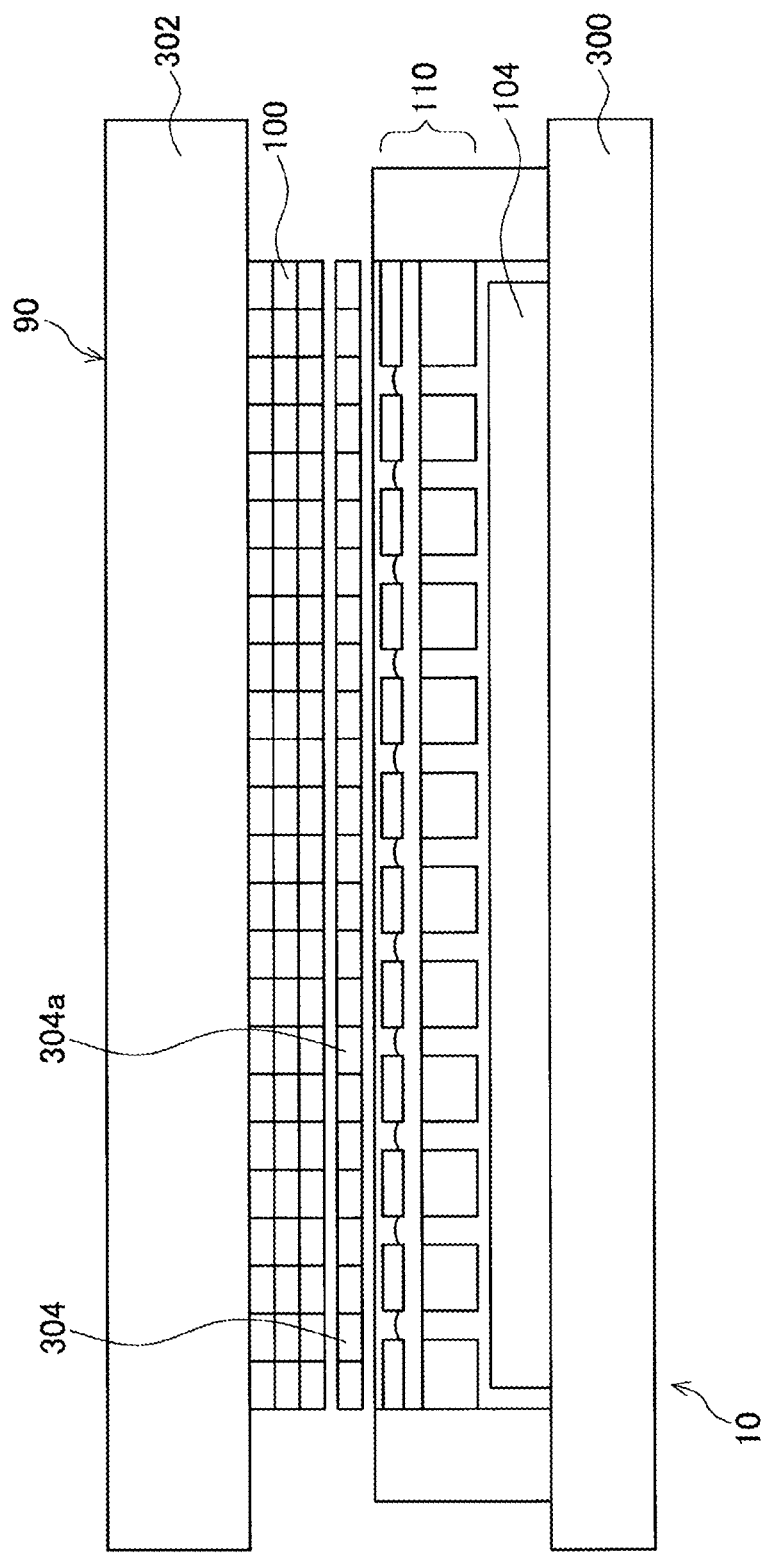

IMAGING APPARATUS AND IMAGING METHOD

CROSS REFERENCE TO RELATED APPLICATIONS

This application is a U.S. National Phase of International Patent Application No. PCT/JP2020/019695 filed on May 18, 2020, which claims priority benefit of Japanese Patent Application No. JP 2019-099714 filed in the Japan Patent Office on May 28, 2019. Each of the above-referenced applications is hereby incorporated herein by reference in its entirety.

FIELD

The present disclosure relates to an imaging apparatus, an imaging method, and a program.

BACKGROUND

Personal authentication using biometric information such as a fingerprint pattern, which is information unique to an individual, has become very important technology for protecting individual rights, assets, and the like in a network society. In particular, in electronic commerce, by performing personal authentication using biometric information such as a fingerprint pattern instead of inputting a password, user convenience is improved while high security is ensured. As an example of such technology, technology disclosed in Patent Literature 1 below can be mentioned.

CITATION LIST

Patent Literature

Patent Literature 1: JP 2017-196319 A

SUMMARY

Technical Problem

In recent years, in order to enable the personal authentication using the biometric information such as the fingerprint pattern in all situations of daily life, downsizing of a sensor (imaging apparatus) that acquires an image related to the biometric information such as the fingerprint pattern is strongly required. Furthermore, even in a case where the sensor is downsized, it is also required to acquire a high-quality image such as the fingerprint pattern in order to accurately perform the personal authentication.

Accordingly, in view of the above circumstances, the present disclosure proposes a new and improved imaging apparatus that can acquire a high-quality image and can realize downsizing, an imaging method, and a program.

Solution to Problem

For solving the problem described above, an imaging apparatus according to one aspect of the present disclosure has an irradiation unit that irradiates a subject with light; an imaging unit that images the subject a plurality of times; a control unit that controls the imaging unit and the irradiation unit; and a combination unit that combines a plurality of imaged images obtained by the imaging unit, wherein the imaging unit has a plurality of imaging elements disposed in a matrix when viewed from the side of the subject, the irradiation unit has a plurality of light emitting elements provided so as to correspond to the plurality of imaging elements, and the control unit controls the irradiation unit so as to turn on the plurality of light emitting elements different for each imaging among the plurality of light emitting elements, and controls the imaging unit so as to drive the plurality of imaging elements corresponding to the plurality of light emitting elements that are not turned on.

An imaging method using an imaging apparatus according to one aspect of the present disclosure, the imaging method, the imaging apparatus including an irradiation unit that irradiates a subject with light, an imaging unit that images the subject a plurality of times, a control unit that controls the imaging unit and the irradiation unit, and a combination unit that combines a plurality of imaged images obtained by the imaging unit, the imaging unit having a plurality of imaging elements disposed in a matrix when viewed from the side of the subject, the irradiation unit having a plurality of light emitting elements provided so as to correspond to the plurality of imaging elements, comprises turning on the plurality of light emitting elements different for each imaging among the plurality of light emitting elements; and driving the plurality of imaging elements corresponding to the plurality of light emitting elements that are not turned on.

A program for causing a computer to realize control of an imaging apparatus according to one aspect of the present disclosure, the imaging apparatus including an irradiation unit that irradiates a subject with light, an imaging unit that images the subject a plurality of times, a control unit that controls the imaging unit and the irradiation unit, and a combination unit that combines a plurality of imaged images obtained by the imaging unit, the imaging unit having a plurality of imaging elements disposed in a matrix when viewed from the side of the subject, the irradiation unit having a plurality of light emitting elements provided so as to correspond to the plurality of imaging elements, causes a computer to function as: a function of turning on the plurality of light emitting elements different for each imaging among the plurality of light emitting elements; and a function of driving the plurality of imaging elements corresponding to the plurality of light emitting elements that are not turned on.

BRIEF DESCRIPTION OF DRAWINGS

FIGS. 29A, 29B, 29C and 29D are explanatory diagrams for explaining an operation example of the authentication device 10 according to the fifth embodiment.

FIG. 30 is an explanatory diagram for explaining a configuration example of a part of an authentication device 10 according to a sixth embodiment of the present disclosure.

DESCRIPTION OF EMBODIMENTS

Figure 1:
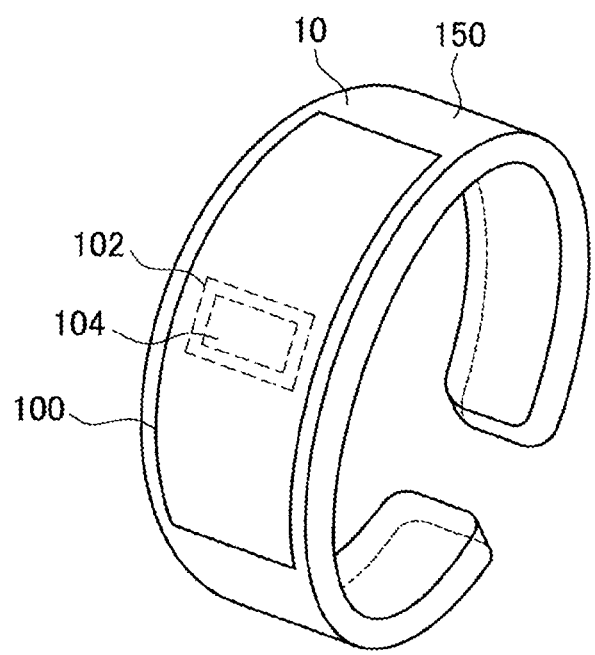
FIG. 1 is a diagram illustrating an example of a form of an authentication device 10 according to a first embodiment of the present disclosure.

Hereinafter, preferred embodiments of the present disclosure will be described in detail with reference to the accompanying drawings. Note that, in the present specification and the drawings, components having substantially the same functional configuration are denoted by the same reference numerals, and redundant description is omitted. Further, in the present specification and the drawings, similar components of different embodiments may be distinguished by adding different alphabets after the same reference numerals. However, when it is unnecessary to particularly distinguish each of the similar components, only the same reference numeral is assigned.

Note that, in the following description, a person who performs personal authentication using an authentication device according to an embodiment of the present disclosure to be described later is referred to as a user.

Further, in the following description, a pattern appearing on a part of a body of the user means, for example, a fingerprint pattern appearing on a fingertip of the user or a vein pattern appearing on various places (a fingertip, a face, and the like) of the body of the user. Further, the fingerprint pattern refers to a pattern formed by a line (ridge) in which an opening of a sweat gland on a surface of a skin on the inner side of the distal end side (fingertip) from a first joint of a finger is raised. The vein pattern refers to a pattern formed by a blood vessel that returns blood from a distal end portion of the body or the like to a heart. Further, in the following description, feature point information of the pattern or feature information of a part of the pattern means information of the pattern or information including information of the feature point included in the pattern.

Further, in the following description, the feature point refers to an element that characterizes the pattern. For example, the feature point in the fingerprint pattern refers to attribute information such as a shape, a direction, and a position (relative coordinates) with respect to a center point of the fingerprint pattern, a branch point of the ridge, an intersection, and an end point (referred to as a minutia). Further, the feature point may be attribute information such as a shape, a direction, a width, an interval, and a distribution density of the ridges. Further, in the following description, the distribution of the feature points, that is, the number or distribution density (distribution information) of the feature points is referred to as a feature amount.

Note that the description will be given in the following order.

1. Background until embodiments of present disclosure are created
2. First Embodiment
2.1 Form of authentication device 10
2.2 Functional configuration example of authentication device 10
2.3 Detailed configuration around fingerprint sensor unit 104
2.4 Authentication method
2.5 Modification
3. Second Embodiment
4. Third Embodiment
4.1 Detailed configuration around fingerprint sensor unit 104
4.2 Modification
5. Fourth Embodiment
6. Fifth Embodiment
7. Sixth Embodiment
8. Seventh Embodiment
9. Application
10. Summary
11. Hardware configuration
12. Supplement

1. Background Until Embodiments of Present Disclosure are Created

Figure 35:
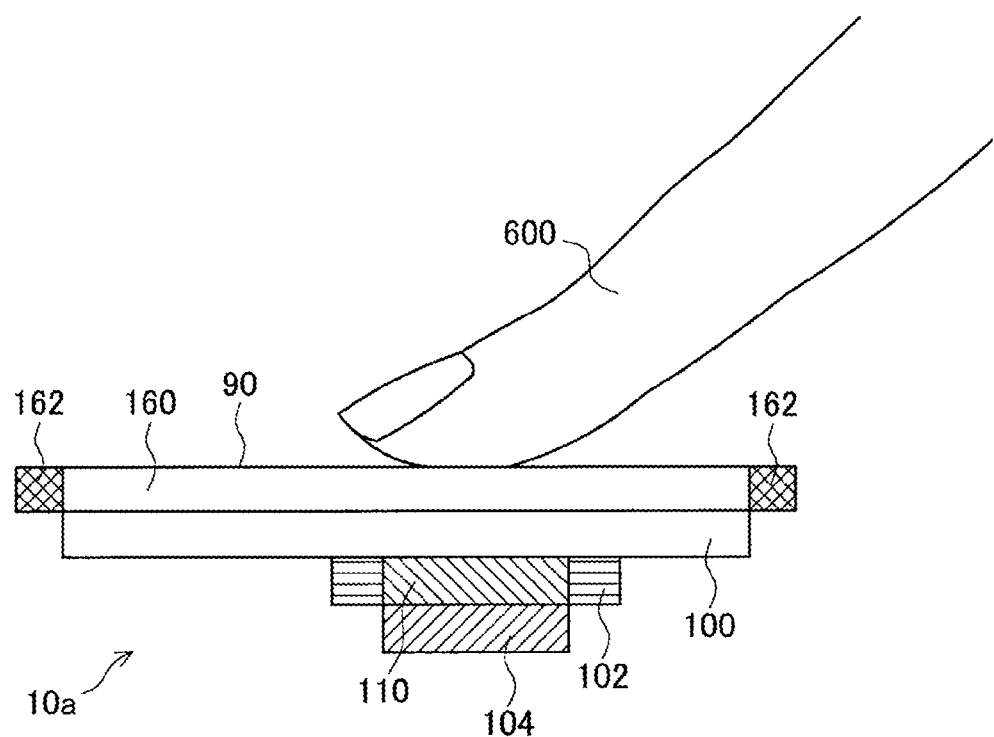
FIG. 35 is an explanatory diagram for explaining a configuration example of a part of an authentication device 10a according to a comparative example.

First, before describing the details of the embodiments of the present disclosure, a background until the embodiments of the present disclosure are created by the present inventors will be described with reference to FIG. 35. FIG. 35 is an explanatory diagram for explaining a configuration example of a part of an authentication device 10a according to a comparative example. Here, the comparative example means a configuration of the authentication device 10a intensively studied by the present inventors before creating the embodiments of the present disclosure.

Meanwhile, as described above, in recent years, for example, downsizing is strongly required for a sensor (imaging apparatus) for acquiring a fingerprint pattern (subject) and the like. Furthermore, in order to accurately perform personal authentication even when the sensor is downsized, the sensor is also required to acquire a high-quality image such as a fingerprint pattern.

The authentication device (imaging apparatus) 10a according to the comparative example capable of acquiring an image of a fingerprint pattern and performing authentication is configured as illustrated in FIG. 35, for example. Specifically, the authentication device 10a has a light guide plate 160 having a placement surface 90 on which a fingertip 600 of a user is placed, and a display unit 100 that is provided below (lower side in the drawing) the light guide plate 160 and displays guidance information for guiding the fingertip 600 of the user to the placement surface 90 for fingerprint authentication. Further, the authentication device 10a has a fingerprint sensor unit 104 that is provided below the display unit 100 and images a fingerprint pattern of the fingertip 600, and a lens unit 110 that guides light reflected by a surface of the fingertip 600 to the fingerprint sensor unit 104. Further, the authentication device 10a has a touch sensor unit 102 that is provided so as to surround the lens unit 110 and the fingerprint sensor unit 104 when viewed from above the placement surface 90 (in other words, when the placement surface 90 is viewed from a direction from the top to the bottom in the drawing), and senses a contact state as to whether or not the fingertip 600 of the user is properly in contact with the placement surface 90. In the authentication device 10a, an irradiation unit 162 that irradiates the surface of the fingertip 600 of the user with light is provided so as to surround the light guide plate 160 when viewed from above the placement surface 90.

As can be seen from FIG. 35, in the authentication device 10a according to the comparative example, the irradiation unit 162 that irradiates the surface of the fingertip 600 with light and the light guide plate 160 that guides the light from the irradiation unit 162 to the fingertip 600 and guides the light reflected by the fingertip 600 to the fingerprint sensor unit 104 are required. Therefore, in the comparative example, the configuration of the authentication device 10a becomes complicated, and it is difficult to downsize the authentication device 10a.

Further, in the comparative example, since the irradiation unit 162 is provided so as to surround the light guide plate 160, a region on the surface of the fingertip 600 close to the irradiation unit 162 is strongly irradiated with light, so that the image of the fingerprint pattern in the region has high brightness. On the other hand, in the region on the surface of the fingertip 600 far from the irradiation unit 162, light is weakly applied according to a distance from the irradiation unit 162, so that the image of the fingerprint pattern in the region has low brightness. Therefore, in the comparative example, since the brightness tends to vary in the image of the fingerprint pattern, it is difficult to acquire a high-quality uniform image for authentication.

Therefore, in view of such a situation, the present inventors have intensively studied an authentication device that can be downsized and can acquire a high-quality image. In addition, in the course of the study, the present inventors have independently focused on using a transparent organic light emitting diode (OLED) device including a transparent organic electro luminescence (EL) element having both a function of displaying (emitting light) and a function of transmitting light. Specifically, the present inventors have independently created an authentication device according to an embodiment of the present disclosure that can be downsized and can acquire a high-quality image by using the display unit 100 including a transparent OLED device instead of the display unit 100, the irradiation unit 162, and the light guide plate 160. Hereinafter, details of embodiments of the present disclosure created by the present inventors will be sequentially described.

2. First Embodiment

<2.1 Form of Authentication Device 10>

First, an example of a form of an authentication device 10 according to a first embodiment of the present disclosure will be described with reference to FIG. 1. FIG. 1 is a diagram illustrating an example of a form of the authentication device 10 according to the present embodiment. The authentication device 10 according to the present embodiment can have a form as a wearable terminal used by being worn on a body of a user, for example. For example, the authentication device 10 may be a device that has a shape of a wristwatch type, a ring type, a collar type, an earphone type, or the like and can be worn on a part of a measured person such as a wrist, an arm, a neck, or an ear. Further, the authentication device 10 may be a device that has a pad shape such as an adhesive plaster and can be attached to a part of the body of the user such as a hand, an arm, a neck, and a leg.

For example, as illustrated in FIG. 1, the authentication device 10 can have a form of a wristwatch type having a belt-like wristband. Specifically, the authentication device 10 has a belt-like band portion 150, a display unit 100 provided on a part of the outer periphery of the band portion 150, and a touch sensor unit 102 provided to overlap with a part of the display unit 100. Further, the authentication device 10 can have a fingerprint sensor unit 104 provided so as to overlap with a part of the display unit 100. In addition, although not illustrated, a control unit 200 (see FIG. 2) or the like that controls the operation of the authentication device 10 may be provided inside the band portion 150. Note that details of the functional units of the authentication device 10 will be described later.

Furthermore, in the present embodiment, the authentication device 10 is not limited to the wearable terminal illustrated in FIG. 1, and may be a mobile terminal such as a smartphone, a mobile phone, a notebook personal computer (PC), a laptop PC, or a camera carried by the user. Alternatively, in the present embodiment, the authentication device 10 may be a stationary terminal such as a desktop PC, a security device installed at a gate or a door, and a server device that provides various medical devices, supplements, cosmetics, and the like.

<2.2 Functional Configuration Example of Authentication Device 10>

Figure 2:
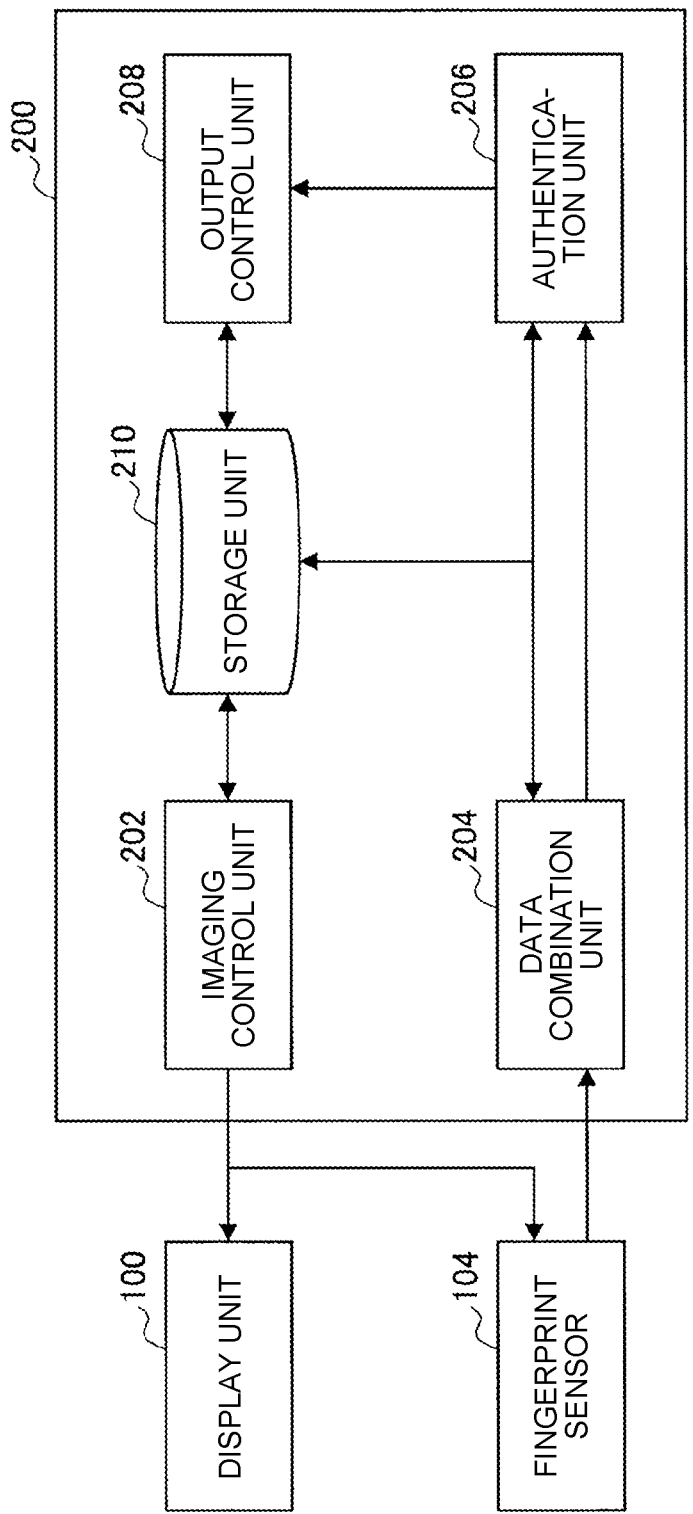
FIG. 2 is a block diagram illustrating a functional configuration example of the authentication device 10 according to the first embodiment.

The form of the authentication device 10 according to the present embodiment has been described above. Next, an example of a functional configuration of the authentication device 10 according to the present embodiment will be described with reference to FIG. 2. FIG. 2 is a block diagram illustrating a functional configuration example of the authentication device 10 according to the present embodiment. As illustrated in FIG. 2, the authentication device 10 mainly has the display unit (irradiation unit) 100, the fingerprint sensor unit (imaging unit) 104, and the control unit 200. Hereinafter, each functional unit included in the authentication device 10 will be described.

(Display Unit 100)

The display unit 100 can display guidance information for guiding a fingertip of the user (a part of the body of the user) (subject) 600 to a placement surface 90 (see FIG. 3) for fingerprint authentication under the control of the control unit 200 described later. Further, the display unit 100 can function as an irradiation unit that irradiates the fingertip 600 of the user with light at the time of acquiring a fingerprint pattern of the fingertip 600 placed on the placement surface 90. The display unit 100 can include, for example, a transparent OLED device having a plurality of transparent organic EL elements (light emitting elements) 100a (see FIG. 4) disposed in a matrix when viewed from above the placement surface 90, that is, when viewed from the side of the subject. Note that a detailed configuration of the display unit 100 will be described later.

(Fingerprint Sensor Unit 104)

The fingerprint sensor unit 104 is provided below the display unit 100 so as to overlap with the display unit 100, for example, and can acquire an image of a fingerprint pattern (subject) of the fingertip 600 of the user placed on the placement surface 90. In the present embodiment, the fingerprint sensor unit 104 can be an optical fingerprint sensor that detects reflected light generated when the fingertip 600 is placed on the placement surface 90 and acquires a fingerprint pattern, and has, for example, a micro lens array (MLA) (micro lens array unit), which is an example of a lens array, and a plurality of imaging elements 104a (see FIG. 4) disposed in a matrix when viewed from above the placement surface 90. Note that a detailed configuration of the fingerprint sensor unit 104 will be described later.

(Control Unit 200)

The control unit 200 can guide the fingertip 600 of the user to an appropriate position on the placement surface 90 for fingerprint authentication, and can perform authentication of the user by the fingerprint in cooperation with the fingerprint sensor unit 104. The control unit 200 is realized by, for example, a central processing unit (CPU), a read only memory (ROM), a random access memory (RAM), and the like. Specifically, as illustrated in FIG. 2, the control unit 200 mainly has an imaging control unit 202, a data combination unit 204, an authentication unit 206, an output control unit 208, and a storage unit 210. Hereinafter, each functional block included in the control unit 200 will be described.

-Imaging Control Unit 202-

The imaging control unit 202 performs drive control related to the display unit 100 and the fingerprint sensor unit 104, and executes acquisition of an image of a fingerprint pattern by the fingerprint sensor unit 104. For example, the imaging control unit 202 controls the plurality of transparent organic EL elements (light emitting elements) 100a (see FIG. 4) of the display unit 100 such that the plurality of transparent organic EL elements 100a different for each imaging are turned on. Further, at this time, the imaging control unit 202 controls the plurality of remaining transparent organic EL elements 100a not turned on such that the plurality of transparent organic EL elements 100a not turned on transmit light. Furthermore, the imaging control unit 202 drives the plurality of imaging elements 104a (see FIG. 4) corresponding to the plurality of transparent organic EL elements 100a not turned on. More specifically, the imaging control unit 202 controls the plurality of imaging elements 104a so as to drive the plurality of imaging elements 104a overlapping with the plurality of transparent organic EL elements 100a not turned on when viewed from above the placement surface 90. Further, at the time of performing control, the imaging control unit 202 may properly refer to various programs, parameters, databases, or the like recorded in the storage unit 210 described later.

-Data Combination Unit 204-

The data combination unit 204 acquires images of fingerprint patterns of a plurality of users from the fingerprint sensor unit 104 described above, combines the images into one image, and outputs the image to the authentication unit 206 described later. Furthermore, the data combination unit 204 may output the combined image to the storage unit 210 described later. Note that the data combination unit 204 may perform predetermined processing on the image of the fingerprint pattern acquired from the fingerprint sensor unit 104 or the combined image to perform emphasis, noise removal, or the like of the fingerprint pattern. More specifically, the data combination unit 204 can use, for example, various filters for smoothing and noise removal such as a moving average filter, a difference filter, a median filter, or a Gaussian filter. Furthermore, the data combination unit 204 may use, for example, various algorithms for binarization and thinning.

-Authentication Unit 206-

The authentication unit 206 can authenticate the user on the basis of feature information of the fingerprint pattern obtained from the combined image of the fingerprint pattern combined by the data combination unit 204. For example, the authentication unit 206 collates the combined image of the fingerprint pattern combined by the data combination unit 204 with a fingerprint template of a fingerprint pattern stored in advance in the storage unit 210, thereby authenticating the user (a pattern matching method). Further, for example, the authentication unit 206 collates a feature point extracted from the combined image with a feature point of a fingerprint pattern stored in advance in the storage unit 210, thereby authenticating the user (a feature point method). Further, for example, the authentication unit 206 slices the combined image into a strip shape, spectrally analyzes a pattern for each sliced pattern, and performs collation using a spectral analysis result of a fingerprint pattern stored in advance in the storage unit 210, thereby performing authentication (a frequency analysis method).

-Output Control Unit 208-

The output control unit 208 performs control related to output of information regarding an authentication result acquired from the authentication unit 206. For example, the output control unit 208 can perform control to cause the display unit 100 described above to display the information regarding the authentication result. Note that the output control unit 208 may properly refer to various programs, parameters, databases, or the like stored in the storage unit 210 described later at the time of performing various types of output control.

-Storage Unit 210-

The storage unit 210 is realized by a random access memory (RAM), a storage device, or the like, and stores programs and various data used for processing in the control unit 200. Specifically, the storage unit 210 stores programs, various data (for example, the above-described fingerprint template, feature point information, and the like), and the like used by the authentication unit 206. In addition to the above data, the storage unit 210 may properly store various parameters that need to be stored when certain processing is performed, processing progress, and the like.

Further, in the present embodiment, the authentication device 10 may include, for example, a voice output device (not illustrated) such as a speaker, may include a lighting device (not illustrated) that notifies the user of predetermined information (authentication result or the like) by flickering or the like, and may have a functional unit such as the touch sensor unit 102 not illustrated in FIG. 2.

Further, in FIG. 2, the authentication device 10 has a configuration in which the fingerprint sensor unit 104 and the like and the control unit 200 are integrated, but the present embodiment is not limited thereto. For example, the authentication device 10 may be configured as an integrated device including the display unit 100 and the fingerprint sensor unit 104, the control unit 200 may be configured as a separate unit, and they may be connected to each other by wireless communication or the like.

<2.3 Detailed Configuration Around Fingerprint Sensor Unit 104>

Figure 3:
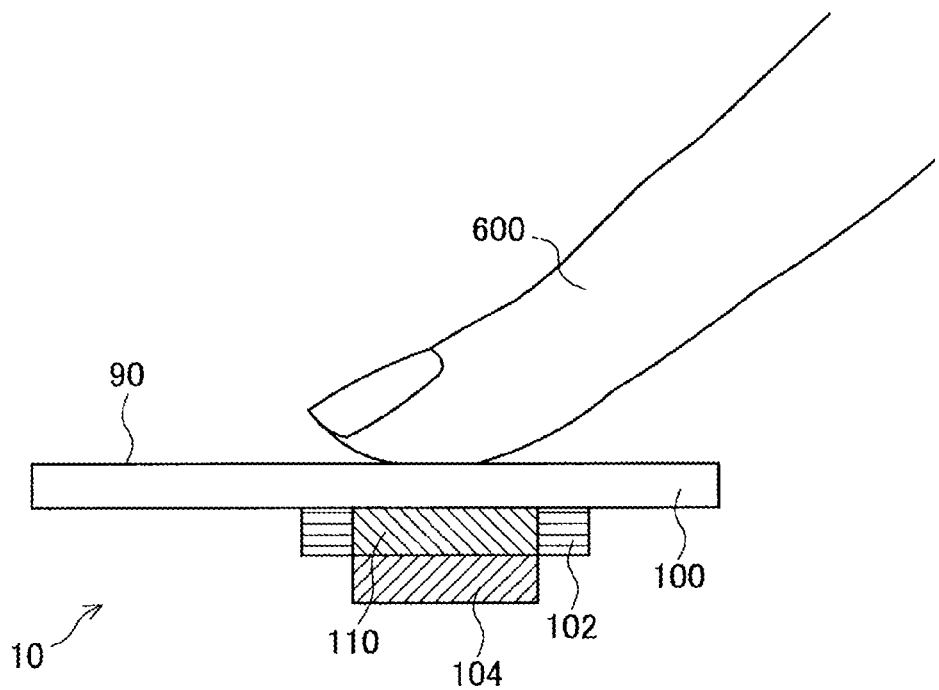
FIG. 3 is an (first) explanatory diagram for explaining a configuration example of a part of the authentication device 10 according to the first embodiment.
Figure 4:
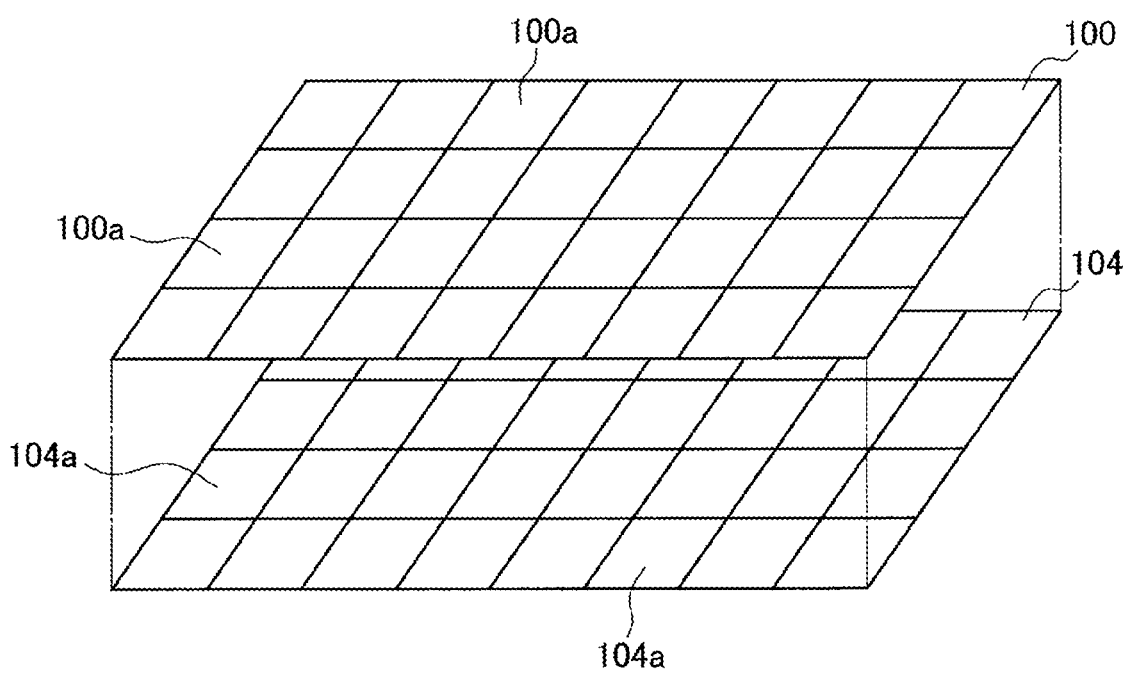
FIG. 4 is an (second) explanatory diagram for explaining a configuration example of a part of the authentication device 10 according to the first embodiment.

The functional configuration of the authentication device 10 according to the present embodiment has been described above. Next, an example of a detailed configuration around the fingerprint sensor unit 104 of the authentication device 10 according to the present embodiment will be described with reference to FIGS. 3 and 4. FIGS. 3 and 4 are explanatory diagrams for explaining a configuration example of a part of the authentication device 10 according to the present embodiment.

As illustrated in FIG. 3, the authentication device 10 according to the present embodiment has the placement surface 90 on which the fingertip 600 of the user is placed. The authentication device 10 has the display unit 100 that is provided below the placement surface 90, functions as an irradiation unit irradiating the surface of the fingertip 600 placed on the placement surface 90 with light, and displays guidance information for guiding the fingertip 600 of the user to the placement surface 90 for fingerprint authentication. Further, the authentication device 10 has the fingerprint sensor unit 104 that is provided below the placement surface 90 so as to overlap with the display unit 100 and images a fingerprint pattern a plurality of times, and the lens unit 110 that guides light reflected by the surface of the fingertip 600 to the fingerprint sensor unit 104. Further, the authentication device 10 has the touch sensor unit 102 that is provided so as to surround the lens unit 110 and the fingerprint sensor unit 104 when viewed from above the placement surface 90 and senses a contact state as to whether or not the fingertip 600 of the user is properly in contact with the placement surface 90. Details of each of these elements will be described below.

(Placement Surface 90)

The placement surface 90 is a surface on which the fingertip 600 of the user is placed, and is preferably a smooth surface with less unevenness in order to avoid giving discomfort to the fingertip 600 of the user, even if the fingertip 600 comes into contact with any position. Further, the placement surface 90 may be formed using a flexible material in order to improve a contact condition with the fingertip 600.

(Display Unit 100)

As illustrated in FIG. 4, the display unit 100 has the plurality of transparent organic EL elements (light emitting elements) 100a disposed in a matrix when viewed from above the placement surface 90. Further, the transparent organic EL elements 100a are disposed so as to correspond to the plurality of imaging elements 104a of the fingerprint sensor unit 104 disposed in a matrix when viewed from above the placement surface 90 (specifically, so as to overlap with each other). More specifically, the display unit 100 has a plurality of light emitting element arrays (not illustrated) each including the plurality of transparent organic EL elements 100a arranged along a horizontal direction or a vertical direction (predetermined direction) in FIG. 4 on the placement surface 90. Further, the display unit 100 has a plurality of light emitting element arrays arranged along the horizontal direction or the vertical direction in FIG. 4 on the placement surface 90. More specifically, in a case where the light emitting element array includes the plurality of transparent organic EL elements 100a arranged along the horizontal direction, the plurality of light emitting element arrays are arranged along the vertical direction. Furthermore, in a case where the light emitting element array includes the plurality of transparent organic EL elements 100a arranged along the vertical direction, the plurality of light emitting element arrays are arranged along the horizontal direction. For example, the transparent organic EL element 100a includes a transparent organic EL element or the like having a transparent upper electrode and a transparent lower electrode that transmit light, and can transmit light at the time of non-light emission.

For example, in the present embodiment, the control unit 200 can cause the plurality of transparent organic EL elements 100a to emit light, and can display guidance information for guiding the fingertip 600 of the user to the placement surface 90 for fingerprint authentication. Further, in the present embodiment, the control unit 200 can perform control such that a plurality of transparent organic EL elements 100a different for each imaging emit light, and the plurality of remaining transparent organic EL elements 100a not turned on transmit light. At this time, the plurality of imaging elements 104a of the fingerprint sensor unit 104 corresponding to the plurality of transparent organic EL elements 100a not turned on can image a part of the fingerprint pattern of the fingertip 600 with the light transmitted through the plurality of remaining transparent organic EL elements 100a not turned on. Note that, in the present embodiment, in each imaging, the plurality of transparent organic EL elements 100a preferably emit light in an irradiation pattern capable of uniformly irradiating the entire placement surface 90 on which the fingertip 600 has been placed with light.

(Touch Sensor Unit 102)

The touch sensor unit 102 can sense, for example, a contact state as to whether or not the fingertip 600 of the user is properly in contact with the placement surface 90. For example, the touch sensor unit 102 can be a pressure sensor or the like that detects a pressure from the fingertip 600.

(Fingerprint Sensor Unit 104)

As illustrated in FIG. 4, the fingerprint sensor unit 104 has the plurality of imaging elements 104a disposed in a matrix form when viewed from above the placement surface 90 so as to correspond to the transparent organic EL elements 100a included in the display unit 100. The imaging element 104a includes, for example, a photodiode, a charge coupled device (CCD) element, a complementary metal oxide semiconductor (CMOS) element, or the like. In the present embodiment, the control unit 200 drives the imaging elements 104a corresponding to the plurality of transparent organic EL elements 100a that are not turned on. At this time, since the light transmitted through the plurality of transparent organic EL elements 100a not turned on is condensed on the driven imaging elements 104a, the fingerprint sensor unit 104 can image a part of the fingerprint pattern of the fingertip 600.

(Lens Unit 110)

Between the display unit 100 and the fingerprint sensor unit 104, the lens unit 110 including a micro lens array (MLA) having a plurality of microlenses (not illustrated) disposed in a matrix when viewed from above the placement surface 90 is provided. Each microlens can guide light incident on the microlens to each imaging element 104a. Therefore, the light reflected by the surface of the fingertip 600 placed on the placement surface 90 is condensed on each imaging element 104a by the microlens to form an image.

As described above, in the present embodiment, by using the display unit 100 including the transparent organic EL element 100a having both the function of displaying (emitting light) and the function of transmitting light, it is possible to omit provision of the irradiation unit 162 included in the authentication device 10a of the comparative example. Further, in the present embodiment, since the display unit 100 and the fingerprint sensor unit 104 can be provided in a stacked manner, the authentication device 10 can be downsized.

<2.4 Authentication Method>

Figure 5:
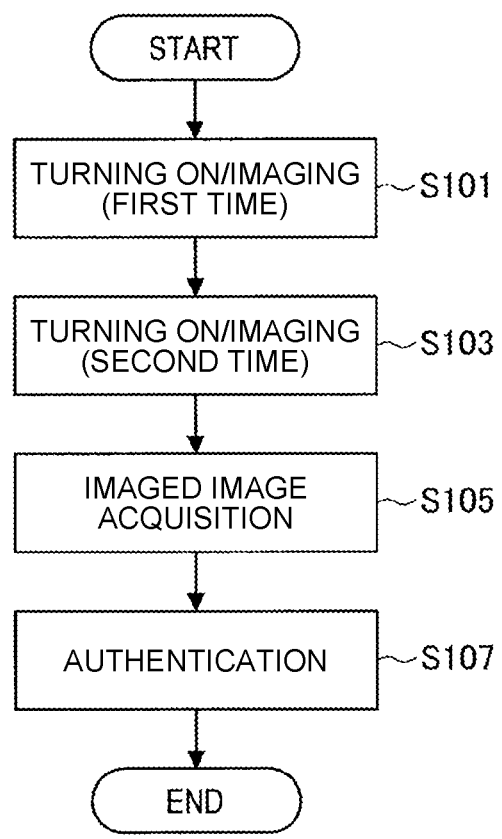
FIG. 5 is a diagram illustrating a flowchart of an authentication method according to the first embodiment.
Figure 6:
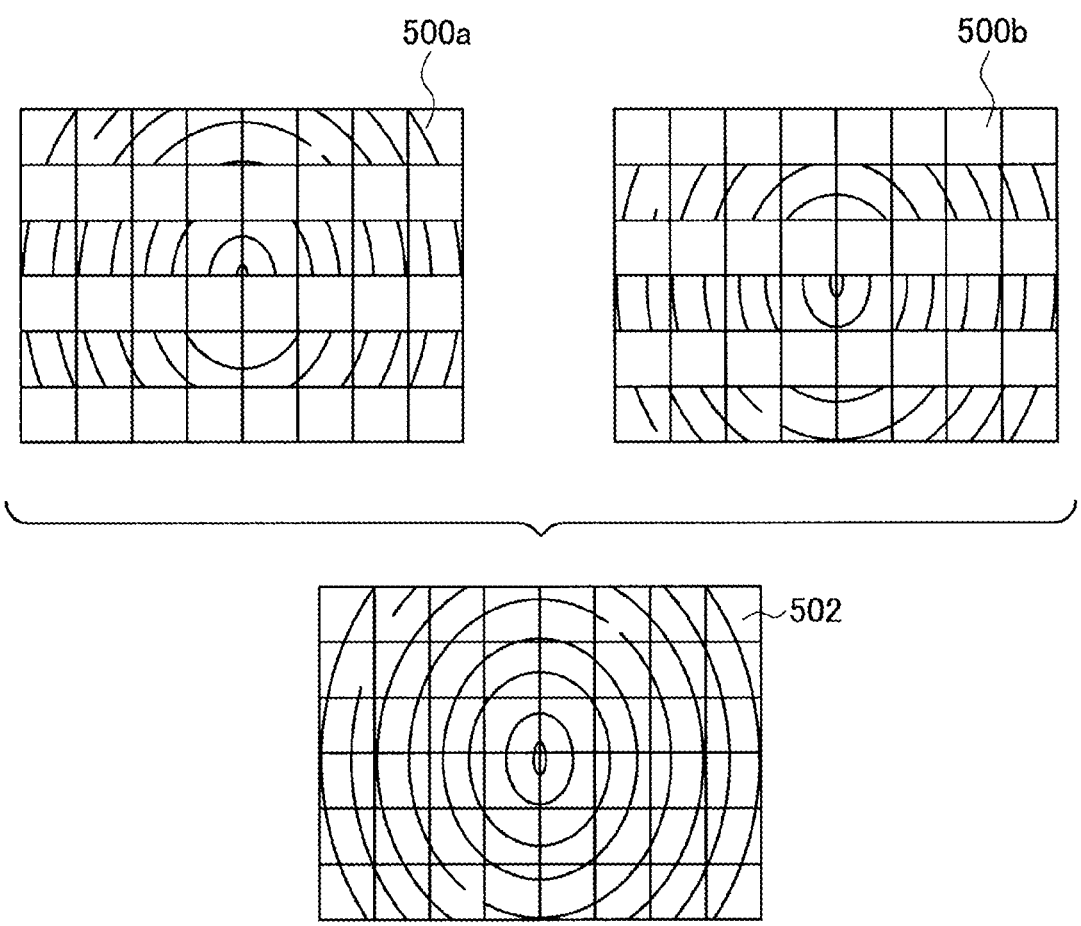
FIG. 6 is an explanatory diagram for explaining an operation example of the authentication device 10 according to the first embodiment.

The detailed configuration of the authentication device 10 according to the present embodiment has been described above. Next, an outline of an authentication method according to the present embodiment will be described with reference to FIGS. 5 and 6. FIG. 5 is a diagram illustrating a flowchart of the authentication method according to the present embodiment. Further, FIG. 6 is an explanatory diagram for explaining an operation example of the authentication device 10 according to the present embodiment.

As illustrated in FIG. 5, the authentication method according to the present embodiment includes steps S101 to S107. Each step of the authentication method according to the present embodiment will be described below. First, before performing authentication, the authentication device 10 displays guidance display (not illustrated) on the display unit 100 toward the user, thereby guiding the fingertip 600 of the user to the placement surface 90.

-Step S101-

The authentication device 10 turns on the plurality of transparent organic EL elements 100a at predetermined positions among the plurality of transparent organic EL elements 100a, and causes the plurality of remaining transparent organic EL elements 100a not turned on to transmit light. Then, the authentication device 10 drives the plurality of imaging elements 104a overlapping with the plurality of transparent organic EL elements 100a that are not turned on when viewed from above the placement surface 90, thereby imaging a part of the fingerprint pattern.

Here, for example, a case where the display unit 100 has a plurality of light emitting element arrays each including the plurality of transparent organic EL elements 100a arranged along the horizontal direction in FIG. 4 on the placement surface 90, and the plurality of light emitting element arrays are arranged along the vertical direction in FIG. 4 (direction perpendicular to the horizontal direction) on the placement surface 90 will be described. In such a case, in step S101, the authentication device 10 controls the plurality of transparent organic EL elements 100a so as to form an irradiation pattern in which each light emitting element array is alternately turned on and turned off (alternately turned on and turned off along the vertical direction). Then, in a case where the irradiation pattern is used, since the plurality of imaging elements 104a overlapping with the plurality of transparent organic EL elements 100a that are not turned on image the fingerprint pattern, in step S101, an imaged image 500a illustrated in the upper left part of FIG. 6 can be acquired. That is, in step S101, the authentication device 10 can obtain the imaged image 500a including an image of one row at an interval of one row along the vertical direction.

-Step S103-

Next, the authentication device 10 turns on the plurality of transparent organic EL elements 100a not turned on in step S101 described above, and causes the plurality of remaining transparent organic EL elements 100a not turned on to transmit light. Then, the authentication device 10 drives the plurality of imaging elements 104a overlapping with the plurality of transparent organic EL elements 100a that are not turned on when viewed from above the placement surface 90, thereby imaging a part of the fingerprint pattern.

For example, in step S103, the authentication device 10 controls the plurality of transparent organic EL elements 100a to form an irradiation pattern in which each light emitting element array is alternately turned on and turned off to turn on the light emitting element arrays not turned on in step S101 described above. When the irradiation pattern is used, in step S103, an imaged image 500b illustrated in the upper right part of FIG. 6 can be acquired. That is, in step S103, the authentication device 10 can obtain the imaged image 500b including an image of one row at an interval of one row along the vertical direction.

In steps S101 and S103 described above, the plurality of transparent organic EL elements 100a provided in a matrix preferably emit light in an irradiation pattern capable of uniformly irradiating the entire placement surface 90 with light. Meanwhile, in the comparative example, as described above, since the region on the surface of the fingertip 600 close to the irradiation unit 162 is strongly irradiated with light, the image of the fingerprint pattern in the region has high brightness. On the other hand, in the region on the surface of the fingertip 600 far from the irradiation unit 162, light is weakly applied according to a distance from the irradiation unit 162, so that the image of the fingerprint pattern in the region has low brightness. Therefore, in the comparative example, the brightness varies in the image of the fingerprint pattern. On the other hand, in the present embodiment, although the fingerprint pattern is imaged twice, in each imaging, the plurality of transparent organic EL elements 100a provided in a matrix can uniformly irradiate the entire placement surface 90 with light from below the placement surface 90. Therefore, variation in brightness hardly occurs in the image of the fingerprint pattern acquired in each imaging, and a high-quality image of a part of the fingerprint pattern image for authentication can be acquired.

-Step S105-

The authentication device 10 acquires the imaged image of the fingerprint pattern imaged in steps S101 and S103 described above. Further, the authentication device 10 combines the two imaged images in a state where respective ends of the acquired imaged images and respective pixels overlap with each other with accuracy, and acquires one combined image. For example, in the present embodiment, the authentication device 10 can combine the imaged images 500a and 500b illustrated in the upper part of FIG. 6 to obtain a combined image 502 illustrated in the lower part of FIG. 6. As described above, in each imaging of steps S101 and S103, only an image of a part of the fingerprint pattern can be acquired although the quality is high. Therefore, in the present embodiment, in step S105, an image of a fingerprint pattern can be acquired by combining imaged images of a part of the two fingerprint patterns imaged in steps S101 and S103.

-Step S107-

The authentication device 10 authenticates the user on the basis of feature information of the combined image of the fingerprint pattern combined in step S105 described above. Note that, in the present embodiment, the authentication method is not particularly limited.

As described above, in the present embodiment, by using the display unit 100 including the transparent organic EL element 100a having both the function of displaying (emitting light) and the function of transmitting light, it is possible to omit provision of the irradiation unit 162 included in the authentication device 10a of the comparative example. Further, in the present embodiment, since the display unit 100 and the fingerprint sensor unit 104 can be provided in a stacked manner, the authentication device 10 can be downsized. Further, in the present embodiment, although the fingerprint pattern is imaged twice, in each imaging, the plurality of transparent organic EL elements 100a provided in a matrix can uniformly irradiate the entire placement surface 90 with light from below the placement surface 90. Therefore, variation in brightness hardly occurs in the image of the fingerprint pattern acquired in each imaging, and a high-quality image of a part of the fingerprint pattern image for authentication can be acquired. Note that, in the present embodiment, an image of a fingerprint pattern can be acquired by combining imaged images of a part of the two imaged fingerprint patterns. That is, according to the present embodiment, it is possible to provide the authentication device 10 that can be downsized and can acquire a high-quality imaged image of a fingerprint pattern.

Note that, in the above description, the example in which the present embodiment is applied to the authentication device 10 that authenticates the user using the image of the fingerprint pattern has been described, but the present embodiment is not limited thereto. For example, the configuration and the operation according to the present embodiment may be applied to an authentication device and an authentication method that authenticate the user using an image of a vein pattern, or may be applied to an imaging apparatus and an imaging method that image a fingerprint pattern, a vein pattern, or the like.

<2.5 Modification>

In the present embodiment, the irradiation pattern in each imaging is not particularly limited as long as light is emitted in an irradiation pattern capable of uniformly irradiating the entire placement surface 90 on which the fingertip 600 is placed with light. In other words, in the present embodiment, the irradiation pattern is not limited to the above-described irradiation pattern as long as the distribution of the transparent organic EL elements 100a turned on around the imaging element 104a that performs imaging is uniform for each imaging element 104a. Therefore, modifications of the present embodiment will be described with reference to FIGS. 7 and 8.

Figure 7:
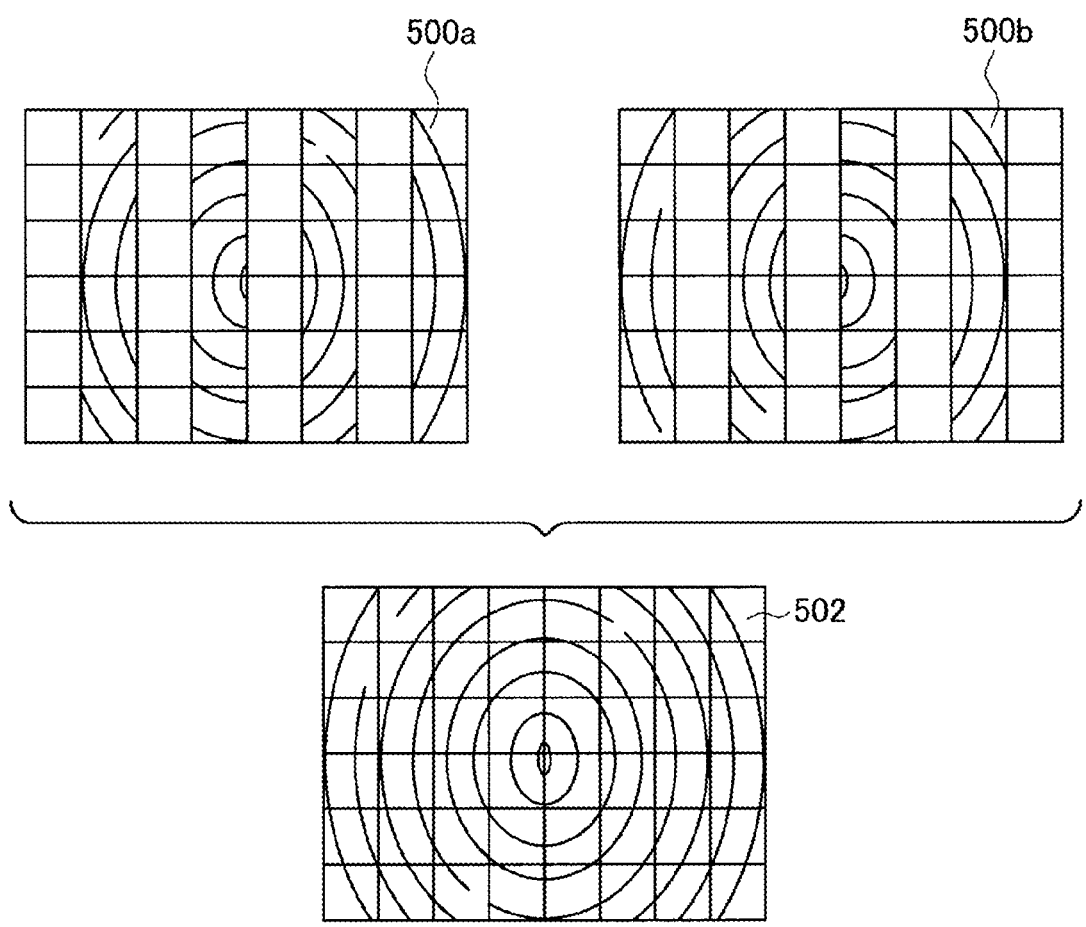
FIG. 7 is an (first) explanatory diagram for explaining an operation example of an authentication device 10 according to a modification of the first embodiment.
Figure 8:
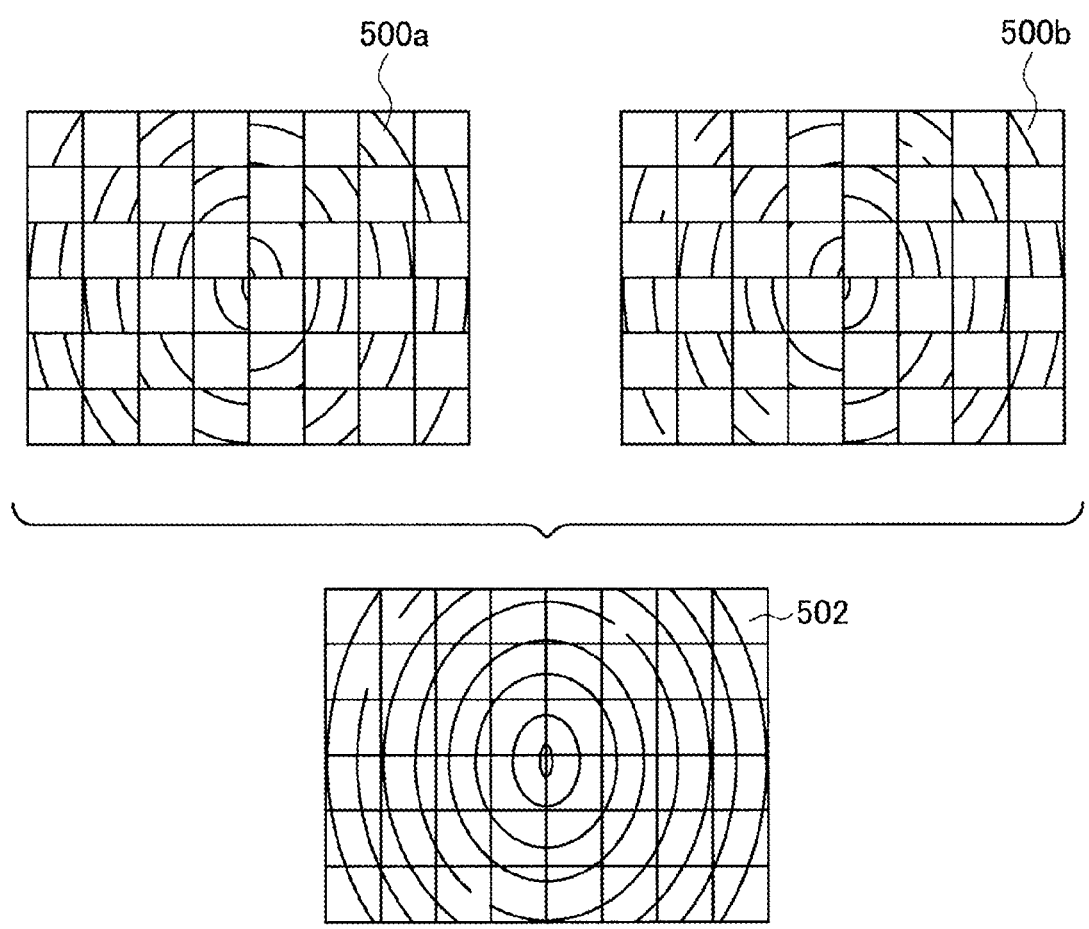
FIG. 8 is an (second) explanatory diagram for explaining an operation example of an authentication device 10 according to a modification of the first embodiment.
Figure 9:
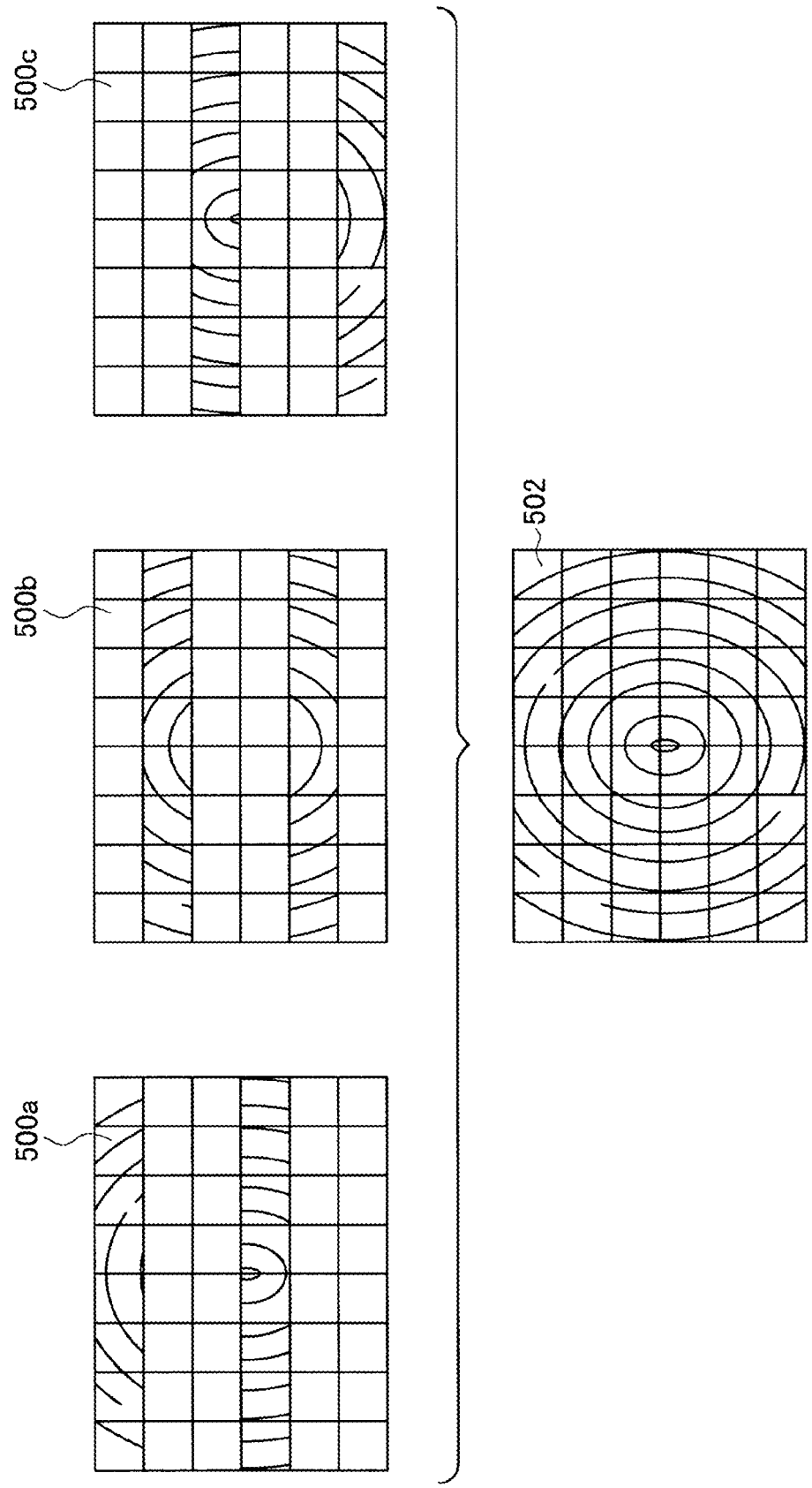
FIG. 9 is an (third) explanatory diagram for explaining an operation example of an authentication device 10 according to a modification of the first embodiment.
Figure 10:
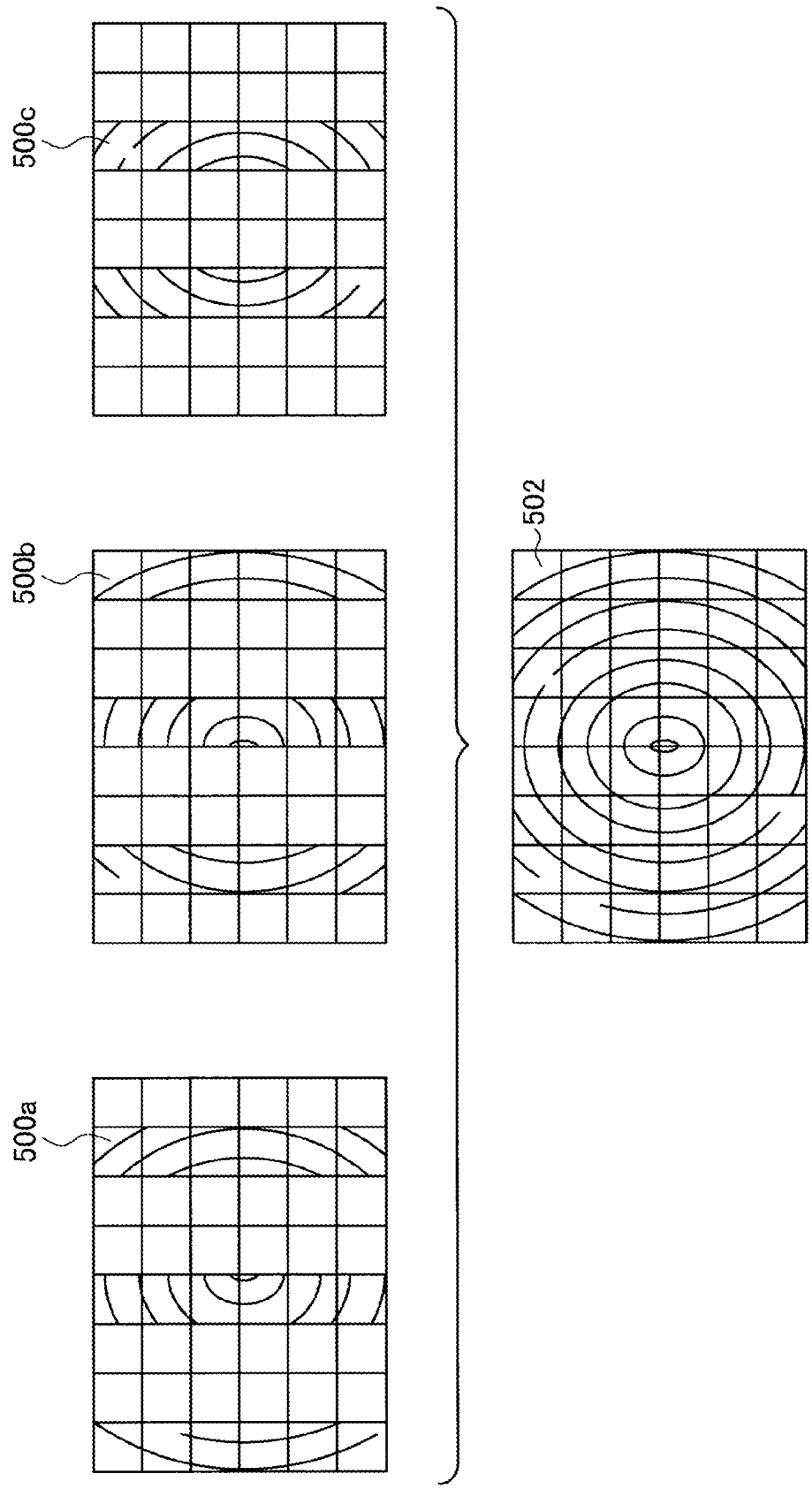
FIG. 10 is an (fourth) explanatory diagram for explaining an operation example of an authentication device 10 according to a modification of the first embodiment.
Figure 11:
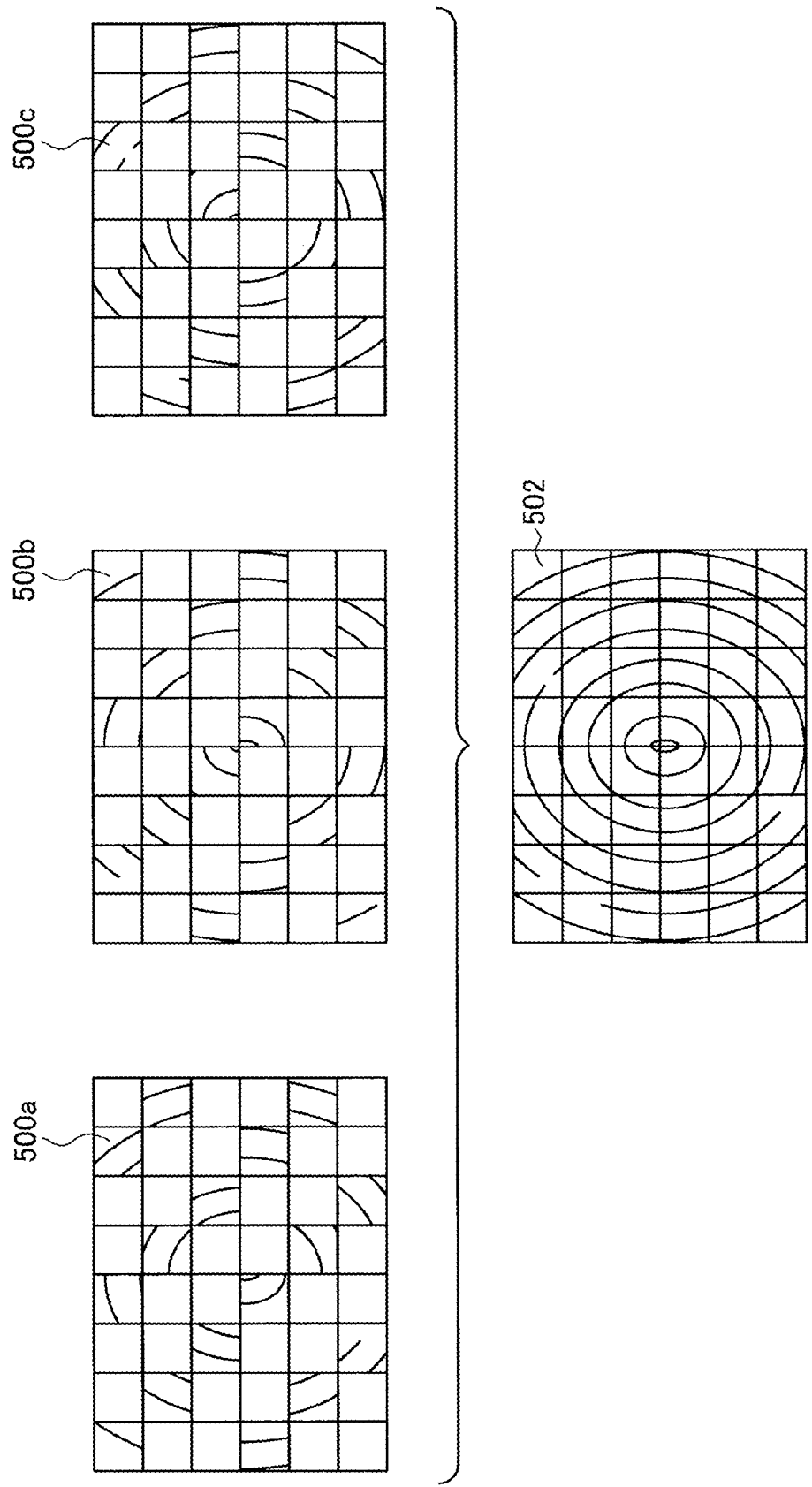
FIG. 11 is an (fifth) explanatory diagram for explaining an operation example of an authentication device 10 according to a modification of the first embodiment.
Figure 12:
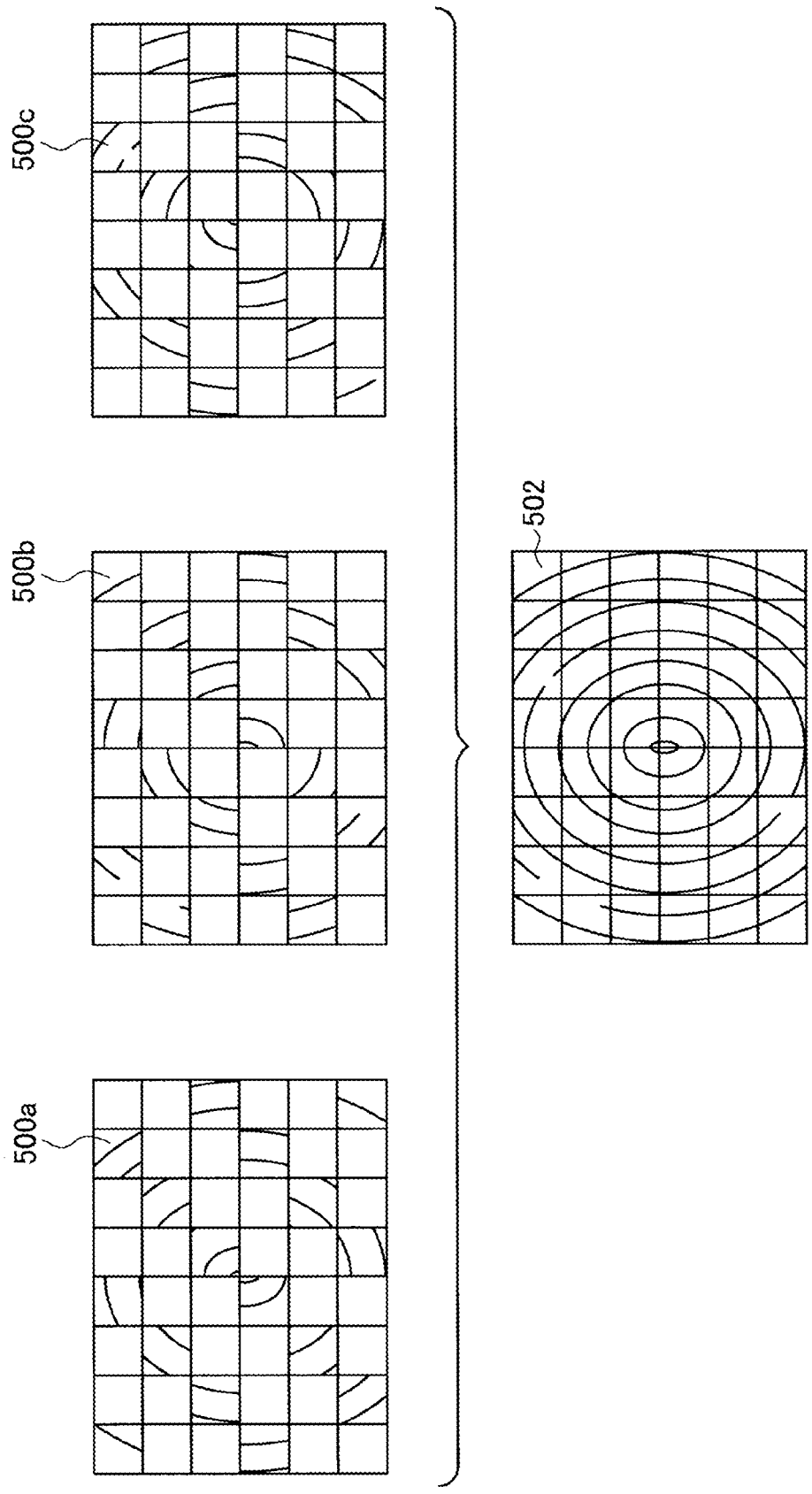
FIG. 12 is an (sixth) explanatory diagram for explaining an operation example of an authentication device 10 according to a modification of the first embodiment.
Figure 13:
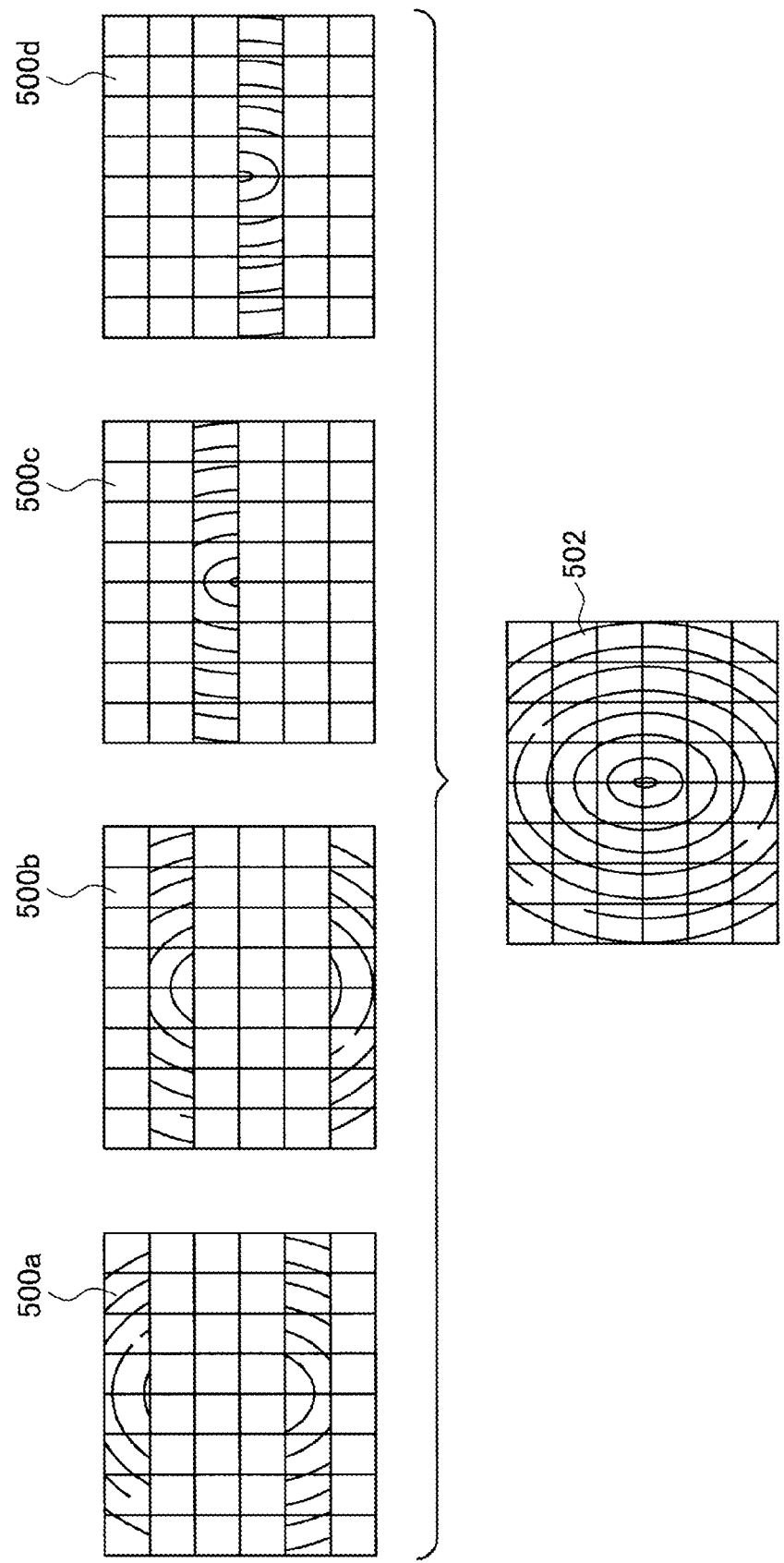
FIG. 13 is an (seventh) explanatory diagram for explaining an operation example of an authentication device 10 according to a modification of the first embodiment.
Figure 14:
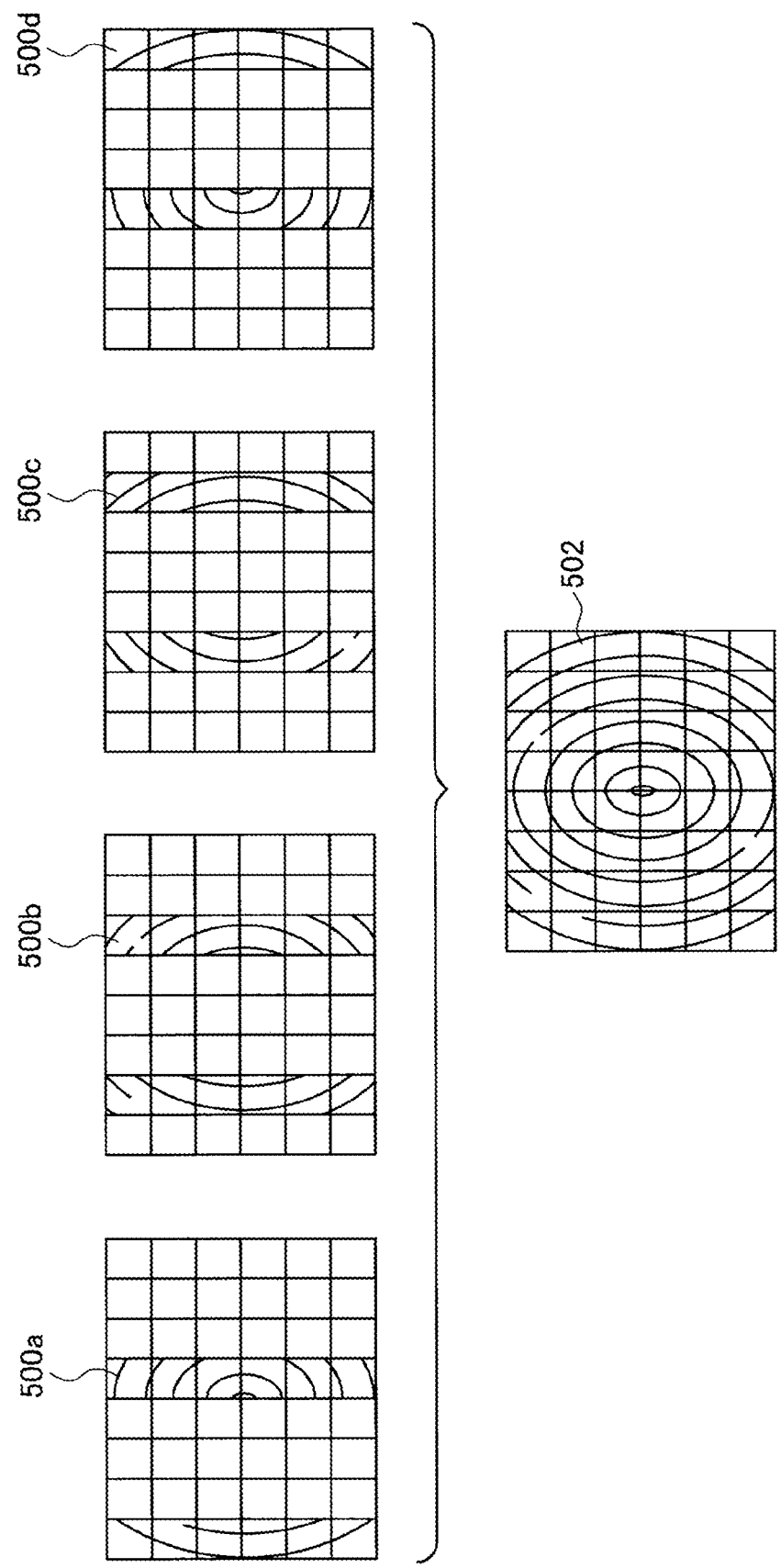
FIG. 14 is an (eighth) explanatory diagram for explaining an operation example of an authentication device 10 according to a modification of the first embodiment.
Figure 15:
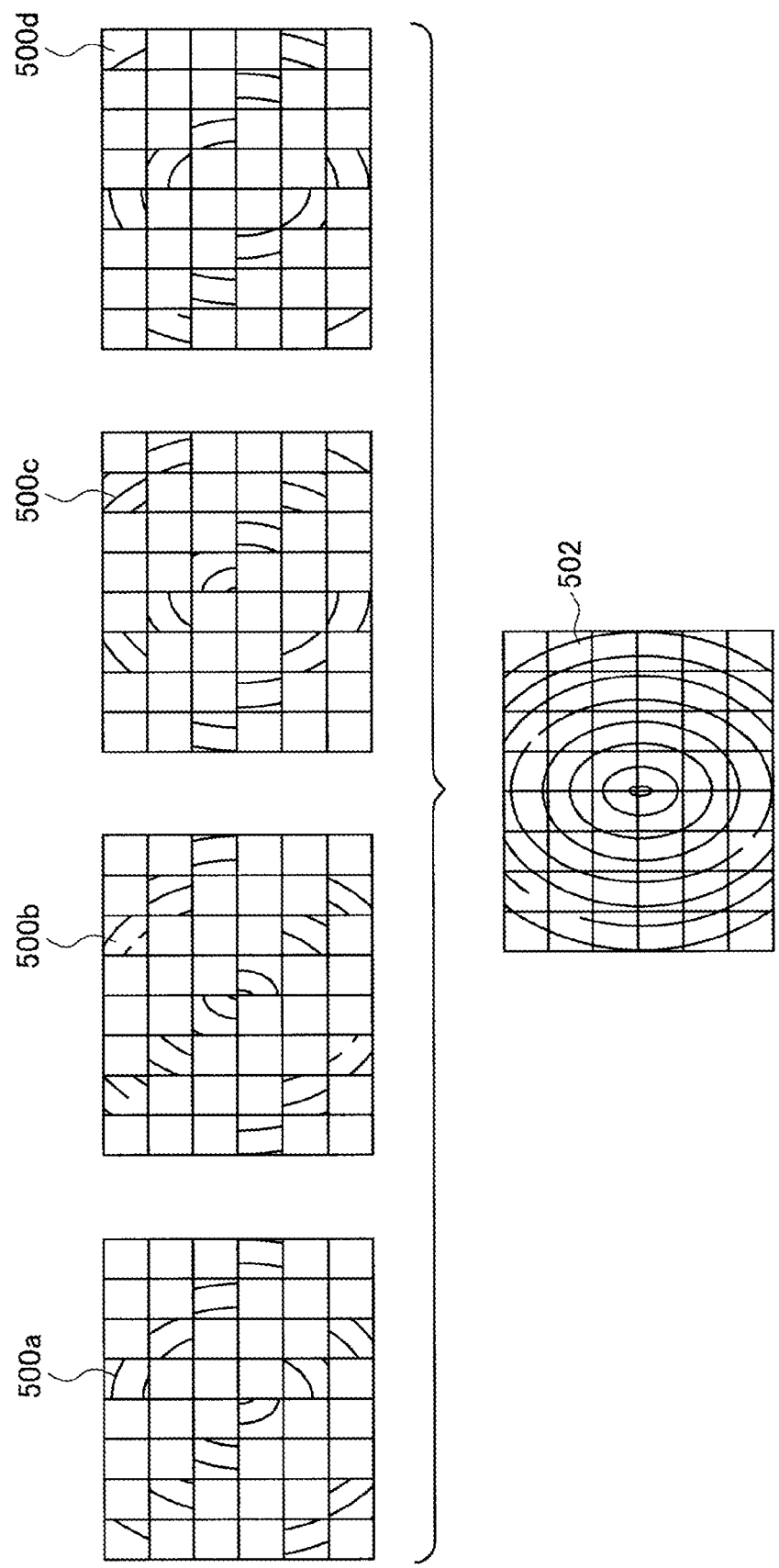
FIG. 15 is an (ninth) explanatory diagram for explaining an operation example of an authentication device 10 according to a modification of the first embodiment.
Figure 16:
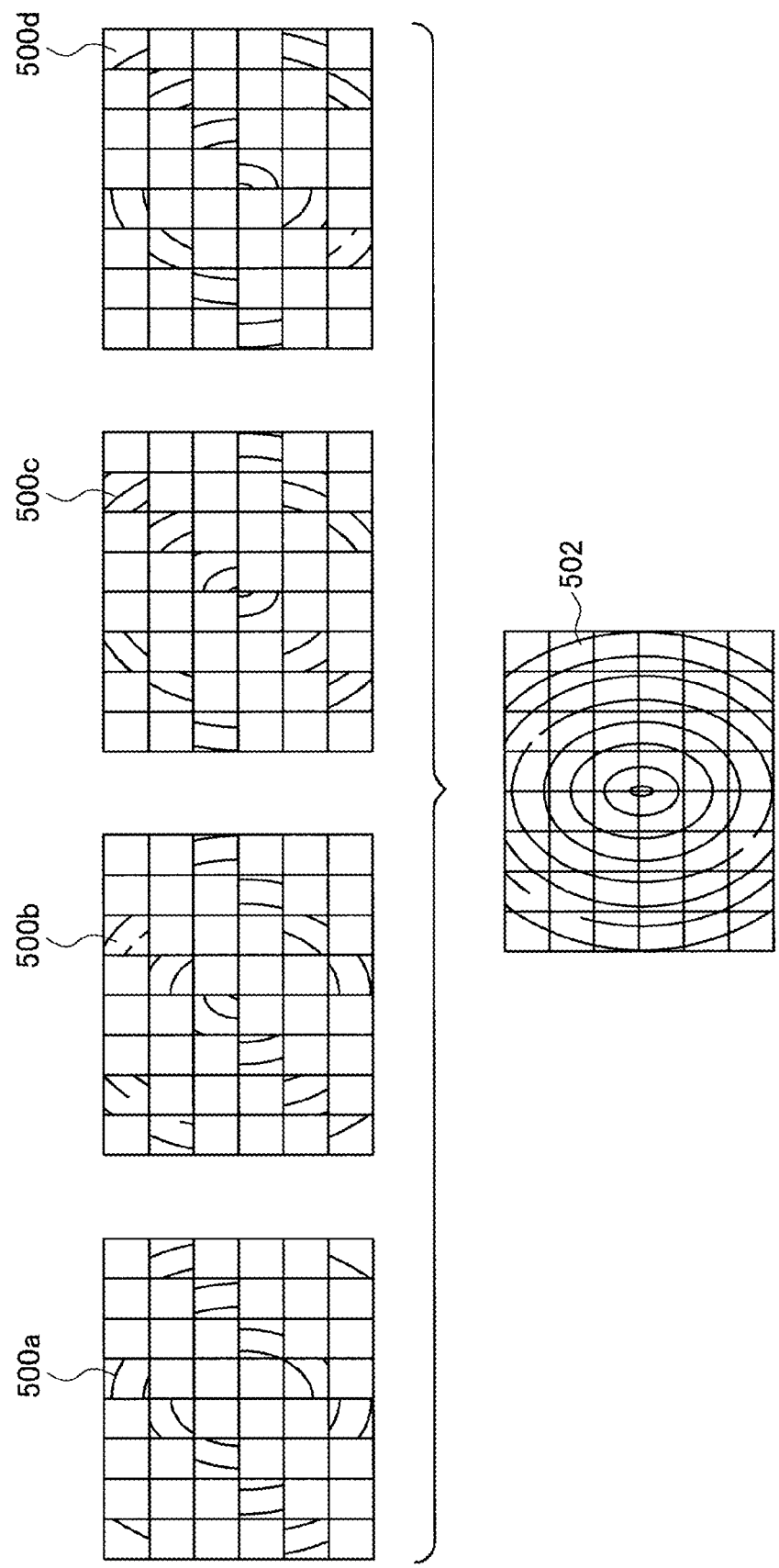
FIG. 16 is an (tenth) explanatory diagram for explaining an operation example of an authentication device 10 according to a modification of the first embodiment.
Figure 17:
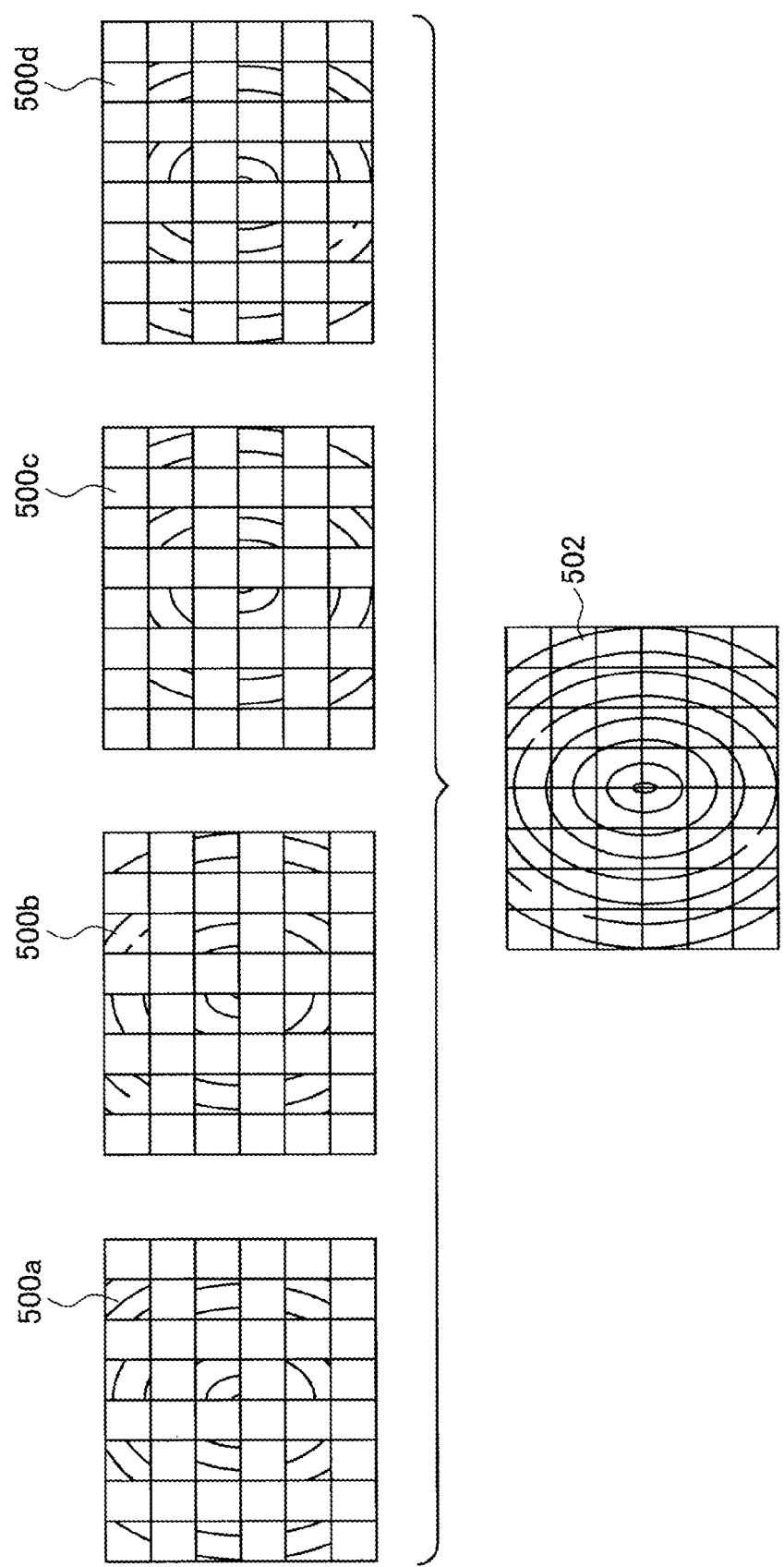
FIG. 17 is an (eleventh) explanatory diagram for explaining an operation example of an authentication device 10 according to a modification of the first embodiment.
Figure 18:
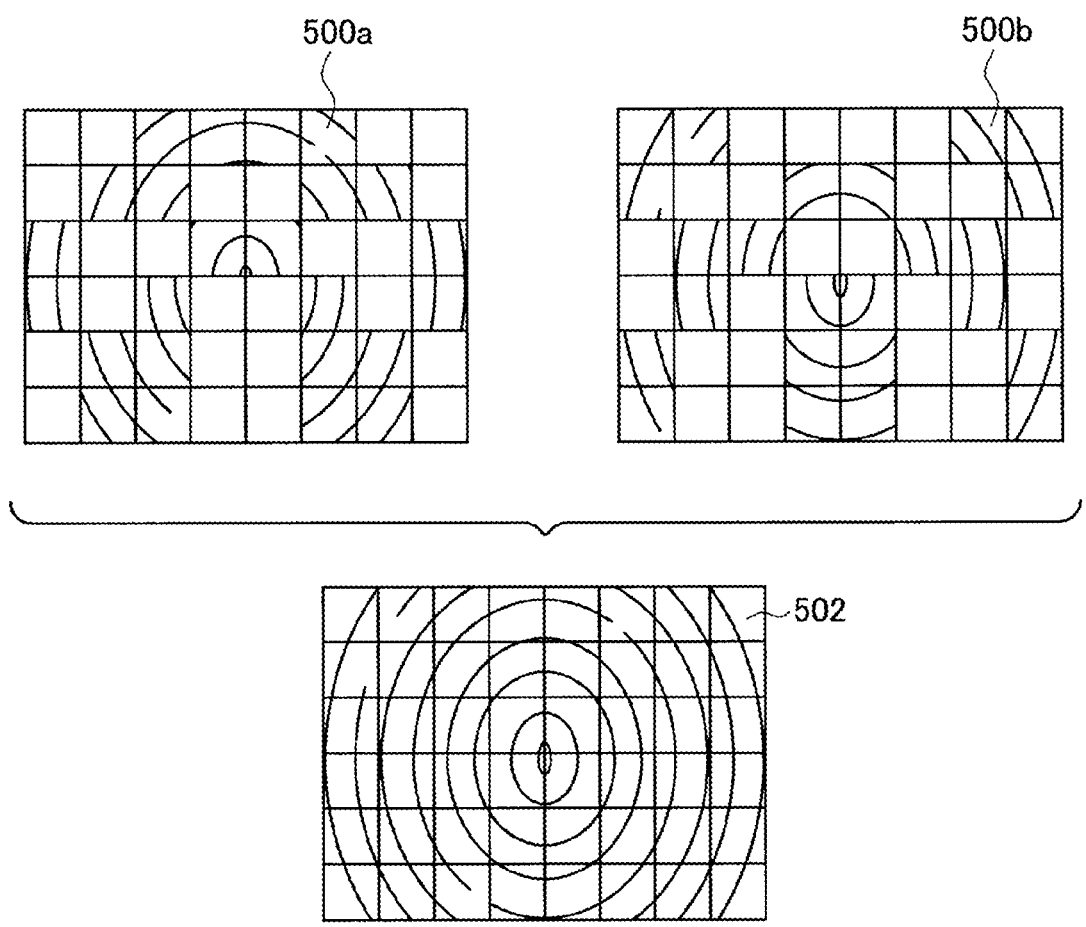
FIG. 18 is an (twelfth) explanatory diagram for explaining an operation example of an authentication device 10 according to a modification of the first embodiment.
Figure 19:
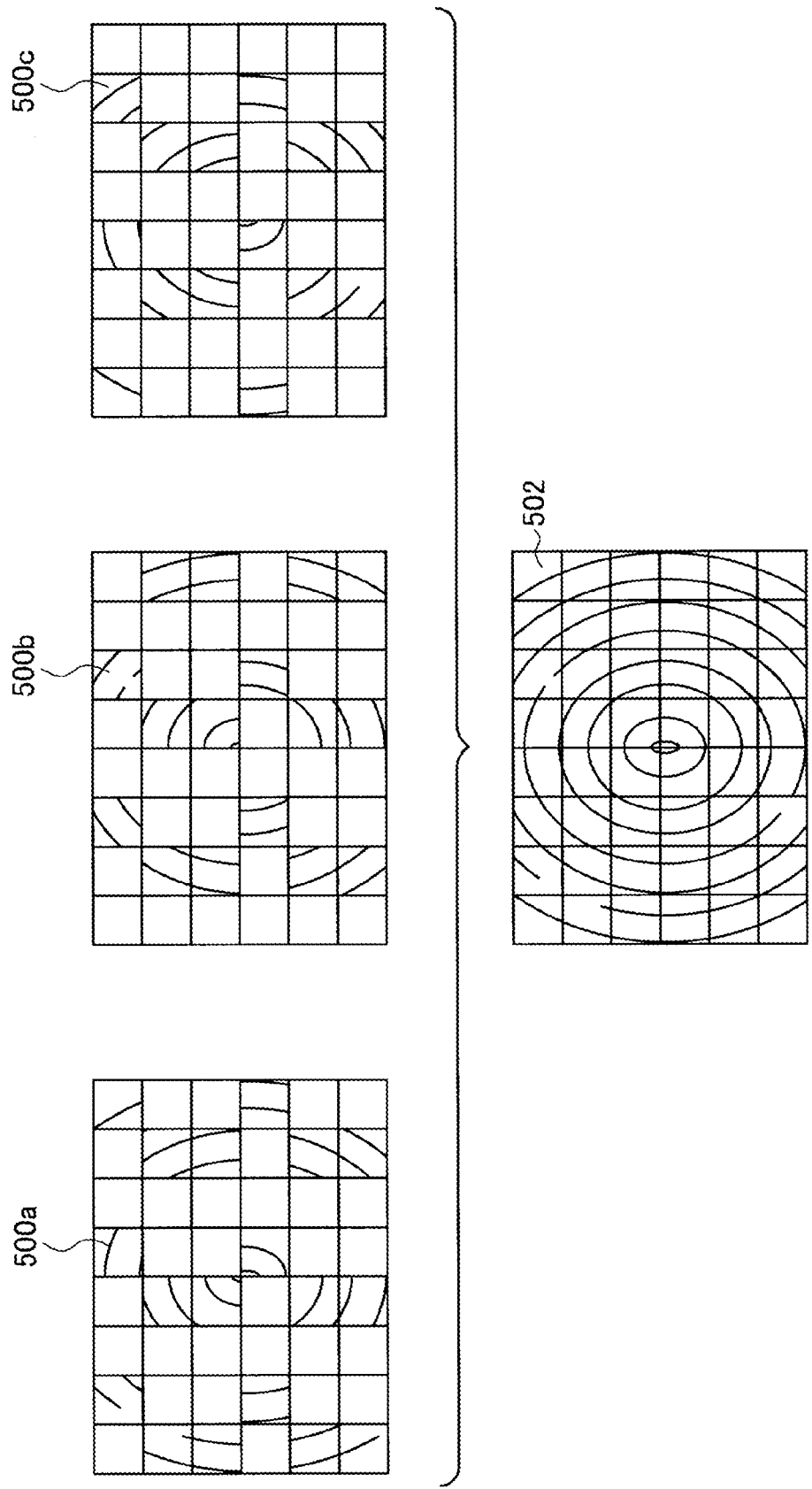
FIG. 19 is an (thirteenth) explanatory diagram for explaining an operation example of an authentication device 10 according to a modification of the first embodiment.
Figure 20:
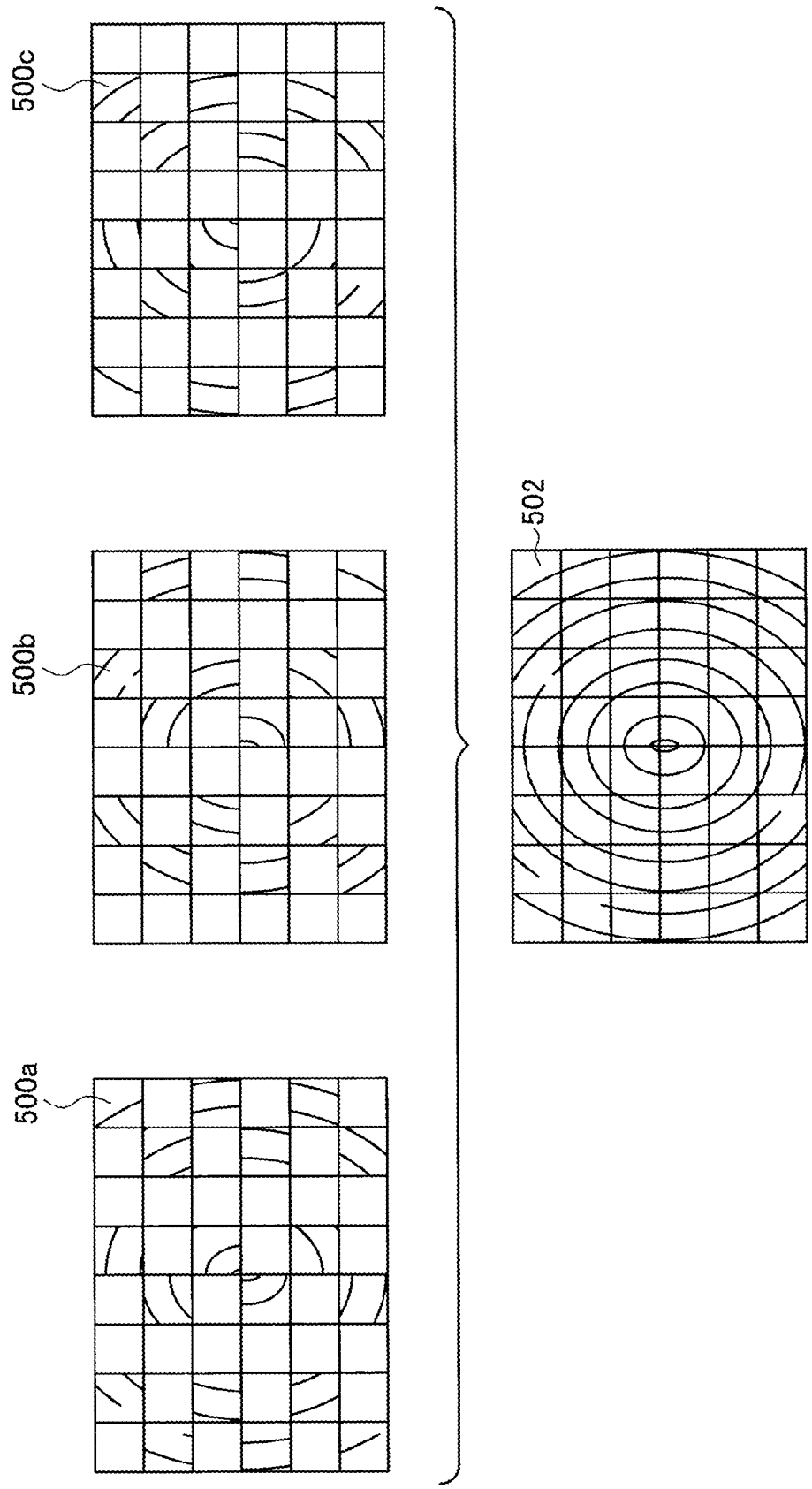
FIG. 20 is an (fourteenth) explanatory diagram for explaining an operation example of an authentication device 10 according to a modification of the first embodiment.
Figure 21:
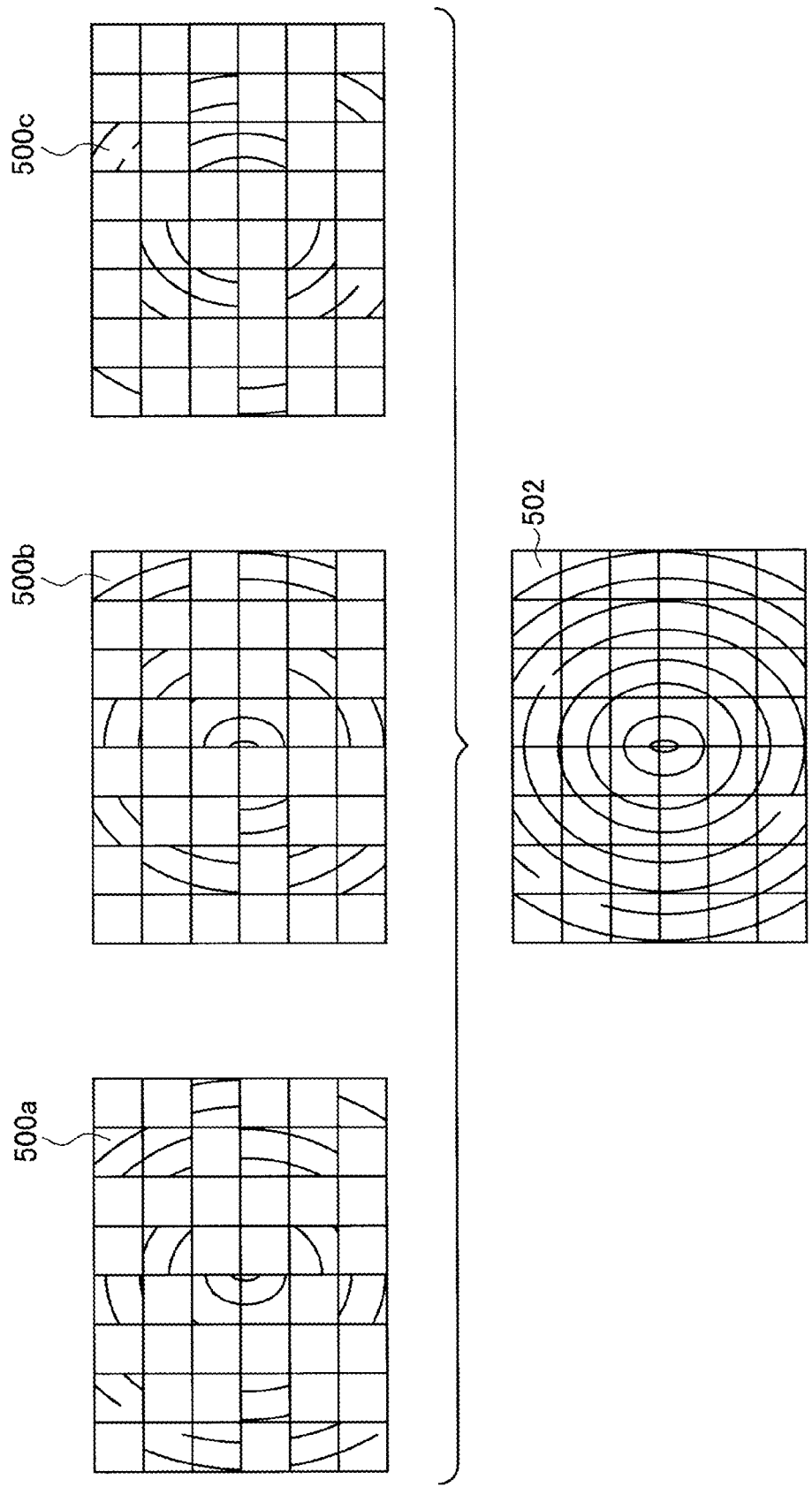
FIG. 21 is an (fifteenth) explanatory diagram for explaining an operation example of an authentication device 10 according to a modification of the first embodiment.

FIGS. 7 and 8 are explanatory diagrams for explaining an operation example of an authentication device 10 according to the modification of the present embodiment.

In the present modification, for example, a case where the display unit 100 has a plurality of light emitting element arrays each including a plurality of transparent organic EL elements 100a arranged along the vertical direction in FIG. 4 on the placement surface 90, and the plurality of light emitting element arrays are arranged along the horizontal direction in FIG. 4 on the placement surface 90 will be described. In such a case, the authentication device 10 may control the plurality of transparent organic EL elements 100a so as to form an irradiation pattern in which each light emitting element array is alternately turned on and turned off (alternately turned on and turned off along the horizontal direction). In such a case, an imaged image 500a illustrated in the upper left part of FIG. 7 can be acquired in first imaging, and an imaged image 500a illustrated in the upper right part of FIG. 7 can be acquired in second imaging. Then, the authentication device 10 can combine the imaged images 500a and 500b illustrated in the upper part of FIG. 7 to obtain a combined image 502 illustrated in the lower part of FIG. 7.

Furthermore, for example, in another modification, the authentication device 10 may control the plurality of transparent organic EL elements 100a so as to form an irradiation pattern in which the transparent organic EL elements 100a are alternately turned on and turned off in a checkered pattern when viewed from above the placement surface 90 in each imaging. In such a case, an imaged image 500a illustrated in the upper left part of FIG. 8 can be acquired in first imaging, and an imaged image 500a illustrated in the upper right part of FIG. 8 can be acquired in second imaging. Then, the authentication device 10 can combine the imaged images 500a and 500b illustrated in the upper part of FIG. 8 to obtain a combined image 502 illustrated in the lower part of FIG. 8.

Further, in the present embodiment, the imaging is not limited to two times as described above, and may be performed a plurality of times such as three times or four times. In this way, since adjustment of the brightness in the imaged image can be finely performed, a higher-quality fingerprint pattern image can be acquired. Therefore, modifications of the present embodiment will be described with reference to FIGS. 9 to 17. FIGS. 9 to 17 are explanatory diagrams for explaining an operation example of an authentication device 10 according to the modification of the present embodiment.

In the present modification, for example, a case where the display unit 100 has a plurality of light emitting element arrays each including a plurality of transparent organic EL elements 100a arranged along the horizontal direction in FIG. 4 on the placement surface 90, and the plurality of light emitting element arrays are arranged along the vertical direction in FIG. 4 on the placement surface 90 will be described. In such a case, the authentication device 10 may control the plurality of transparent organic EL elements 100a so as to form an irradiation pattern in which one light emitting element array and two light emitting element arrays are alternately turned off and turned on. In such a case, an imaged image 500a illustrated in the upper left part of FIG. 9 can be acquired in first imaging, an imaged image 500b illustrated in the upper center of FIG. 9 can be acquired in second imaging, and an imaged image 500c illustrated in the upper right part of FIG. 9 can be acquired in third imaging. Then, the authentication device 10 can combine the imaged images 500a, 500b, and 500c illustrated in the upper part of FIG. 9 to obtain a combined image 502 illustrated in the lower part of FIG. 9.

Further, in the present modification, a case where the display unit 100 has a plurality of light emitting element arrays each including a plurality of transparent organic EL elements 100a arranged along the vertical direction in FIG. 4 on the placement surface 90, and the plurality of light emitting element arrays are arranged along the horizontal direction in FIG. 4 on the placement surface 90 will be described. In such a case, the authentication device 10 may control the plurality of transparent organic EL elements 100a so as to form an irradiation pattern in which one light emitting element array and two light emitting element arrays are alternately turned off and turned on. In such a case, an imaged image 500a illustrated in the upper left part of FIG. 10 can be acquired in first imaging, an imaged image 500b illustrated in the upper center of FIG. 10 can be acquired in second imaging, and an imaged image 500c illustrated in the upper right part of FIG. 10 can be acquired in third imaging. Then, the authentication device 10 can combine the imaged images 500a, 500b, and 500c to obtain a combined image 502.

Further, a case where the display unit 100 has a plurality of light emitting element arrays each including a plurality of transparent organic EL elements 100a arranged along a direction from the upper left end to the lower right end in FIG. 4 on the placement surface 90, and the plurality of light emitting element arrays are arranged along a direction from the upper right end to the lower left end in FIG. 4 on the placement surface 90 will be described. In the present modification, the authentication device 10 may control the plurality of transparent organic EL elements 100a so as to form an irradiation pattern in which one light emitting element array and two light emitting element arrays are alternately turned off and turned on. In such a case, an imaged image 500a illustrated in the upper left part of FIG. 11 can be acquired in first imaging, an imaged image 500b illustrated in the upper center of FIG. 11 can be acquired in second imaging, and an imaged image 500c illustrated in the upper right part of FIG. 11 can be acquired in third imaging. Then, the authentication device 10 can combine the imaged images 500a, 500b, and 500c to obtain a combined image 502.

Further, a case where the display unit 100 has a plurality of light emitting element arrays each including a plurality of transparent organic EL elements 100a arranged along a direction from the upper right end to the lower left end in FIG. 4 on the placement surface 90, and the plurality of light emitting element arrays are arranged along a direction from the upper left end to the lower right end in FIG. 4 on the placement surface 90 will be described. In the present modification, the authentication device 10 may control the plurality of transparent organic EL elements 100a so as to form an irradiation pattern in which one light emitting element array and two light emitting element arrays are alternately turned off and turned on. In such a case, an imaged image 500a illustrated in the upper left part of FIG. 12 can be acquired in first imaging, an imaged image 500b illustrated in the upper center of FIG. 12 can be acquired in second imaging, and an imaged image 500c illustrated in the upper right part of FIG. 12 can be acquired in third imaging. Then, in such a case, the authentication device 10 can combine the imaged images 500a, 500b, and 500c to obtain a combined image 502.

Further, a case where the display unit 100 has a plurality of light emitting element arrays each including a plurality of transparent organic EL elements 100a arranged along the horizontal direction in FIG. 4 on the placement surface 90, and the plurality of light emitting element arrays are arranged along the vertical direction in FIG. 4 on the placement surface 90 will be described. In the present modification, the authentication device 10 may control the plurality of transparent organic EL elements 100a so as to form an irradiation pattern in which one light emitting element array and three light emitting element arrays are alternately turned on and turned off. In such a case, the authentication device 10 can acquire an imaged image 500a illustrated in the upper left part of FIG. 13 in first imaging, and can acquire an imaged image 500b illustrated in the upper center left part of FIG. 13 in second imaging. Then, the authentication device 10 can acquire an imaged image 500c illustrated in the upper center right part of FIG. 13 in third imaging, and can acquire an imaged image 500d illustrated in the upper right part of FIG. 13 in fourth imaging. Then, in such a case, the authentication device 10 can combine the imaged images 500a, 500b, 500c, and 500d illustrated in the upper part of FIG. 13 to obtain a combined image 502 illustrated in the lower part of FIG. 13.

Further, a case where the display unit 100 has a plurality of light emitting element arrays each including a plurality of transparent organic EL elements 100a arranged along the vertical direction in FIG. 4 on the placement surface 90, and the plurality of light emitting element arrays are arranged along the horizontal direction in FIG. 4 on the placement surface 90 will be described. In the present modification, the authentication device 10 may control the plurality of transparent organic EL elements 100a so as to form an irradiation pattern in which one light emitting element array and three light emitting element arrays are alternately turned off and turned on. In such a case, the authentication device 10 can acquire an imaged image 500a illustrated in the upper left part of FIG. 14 in first imaging, and can acquire an imaged image 500b illustrated in the upper center left part of FIG. 14 in second imaging. Then, the authentication device 10 can acquire an imaged image 500c illustrated in the upper center right part of FIG. 14 in third imaging, and can acquire an imaged image 500d illustrated in the upper right part of FIG. 14 in fourth imaging. Then, in such a case, the authentication device 10 can combine the imaged images 500a, 500b, 500c, and 500d to obtain a combined image 502.

Further, a case where the display unit 100 has a plurality of light emitting element arrays each including a plurality of transparent organic EL elements 100*a* arranged along a direction from the upper left end to the lower right end in FIG. 4 on the placement surface 90, and the plurality of light emitting element arrays are arranged along a direction from the upper right end to the lower left end in FIG. 4 on the placement surface 90 will be described. In the present modification, the authentication device 10 may control the plurality of transparent organic EL elements 100*a* so as to form an irradiation pattern in which one light emitting element array and three light emitting element arrays are alternately turned off and turned on. In such a case, the authentication device 10 can acquire an imaged image 500*a* illustrated in the upper left part of FIG. 15 in first imaging, and can acquire an imaged image 500*b* illustrated in the upper center left part of FIG. 15 in second imaging. Then, the authentication device 10 can acquire an imaged image 500*c* illustrated in the upper center right part of FIG. 15 in third imaging, and can acquire an imaged image 500*d* illustrated in the upper right part of FIG. 15 in fourth imaging. Then, in such a case, the authentication device 10 can combine the imaged images 500*a*, 500*b*, 500*c*, and 500*d* to obtain a combined image 502.

For example, a case where the display unit 100 has a plurality of light emitting element arrays each including a plurality of transparent organic EL elements 100*a* arranged along a direction from the upper right end to the lower left end in FIG. 4 on the placement surface 90, and the plurality of light emitting element arrays are arranged along a direction from the upper left end to the lower right end in FIG. 4 on the placement surface 90 will be described. In the present modification, the authentication device 10 may control the plurality of transparent organic EL elements 100*a* so as to form an irradiation pattern in which one light emitting element array and three light emitting element arrays are alternately turned off and turned on. In such a case, the authentication device 10 can acquire an imaged image 500*a* illustrated in the upper left part of FIG. 16 in first imaging, and can acquire an imaged image 500*b* illustrated in the upper center left part of FIG. 16 in second imaging. Then, the authentication device 10 can acquire an imaged image 500*c* illustrated in the upper center right part of FIG. 16 in third imaging, and can acquire an imaged image 500*d* illustrated in the upper right part of FIG. 16 in fourth imaging. Then, in such a case, the authentication device 10 can combine the imaged images 500*a*, 500*b*, 500*c*, and 500*d* to obtain a combined image 502.

Further, a case where the display unit 100 has a plurality of light emitting element arrays each including a plurality of transparent organic EL elements 100*a* arranged along the vertical direction in FIG. 4 on the placement surface 90, and the plurality of light emitting element arrays are arranged along the horizontal direction in FIG. 4 on the placement surface 90 will be described. In the present modification, the authentication device 10 alternately turns on and turns off each light emitting element array, but performs control to form an irradiation pattern in which each transparent organic EL element 100*a* is alternately turned on and turned off in one light emitting element array to be turned on. In such a case, the authentication device 10 can acquire an imaged image 500*a* illustrated in the upper left part of FIG. 17 in first imaging, and can acquire an imaged image 500*b* illustrated in the upper center left part of FIG. 17 in second imaging. Then, the authentication device 10 can acquire an imaged image 500*c* illustrated in the upper center right part of FIG. 17 in third imaging, and can acquire an imaged image 500*d* illustrated in the upper right part of FIG. 17 in fourth imaging. Then, in such a case, the authentication device 10 can combine the imaged images 500*a*, 500*b*, 500*c*, and 500*d* to obtain a combined image 502.

Further, in the present embodiment, an arbitrary pattern may be used instead of the regular irradiation pattern described above, and there is no particular limitation as long as an arbitrary irradiation pattern can uniformly irradiate the entire placement surface 90 on which the fingertip 600 is placed with light. For example, by using various arbitrary irradiation patterns, it is possible to acquire the imaged images 500*a* to 500*c* of the part of the fingerprint pattern as illustrated in the upper parts of FIGS. 18 to 21 which are the explanatory diagrams for explaining the operation example of the authentication device 10 according to the modification of the present embodiment. Then, by combining the imaged images 500*a* to 500*c* of the part of the fingerprint pattern, the combined image 502 illustrated in the lower part of each drawing can be acquired.

Further, in the embodiment and the modifications described above, the images of the part of the fingerprint pattern acquired in each imaging are different from each other, but the present embodiment is not limited thereto. For example, in a case where a high-quality image of the center region of the fingerprint pattern is required for authentication, in the present embodiment, an image of the center region of the fingerprint pattern may be acquired in each imaging and these images may be combined so as to overlap with each other, thereby acquiring an image in which the center region has been more emphasized.

3. Second Embodiment

In the embodiment of the present disclosure described above, an entire placement surface 90 on which a fingertip 600 is placed is uniformly irradiated with light by a plurality of transparent organic EL elements 100*a* disposed in a matrix, so that a high-quality image for authentication can be acquired. However, a surface of the fingertip 600 is a curved surface, and the entire surface of the fingertip 600 is not always in uniform contact with the placement surface 90. Therefore, depending on a contact state of the surface of the fingertip 600, it is not always possible to obtain an image of a fingerprint pattern having uniform brightness over an entire region. Further, in a case where an arbitrary irradiation pattern is used as in the modification described above, since a distribution of the turned-on transparent organic EL elements 100*a* is slightly different for each place, there is a possibility that the brightness varies in the obtained fingerprint pattern image. Furthermore, even when the placement surface 90 is dirty, the brightness may vary in the obtained fingerprint pattern image.

Figure 22:
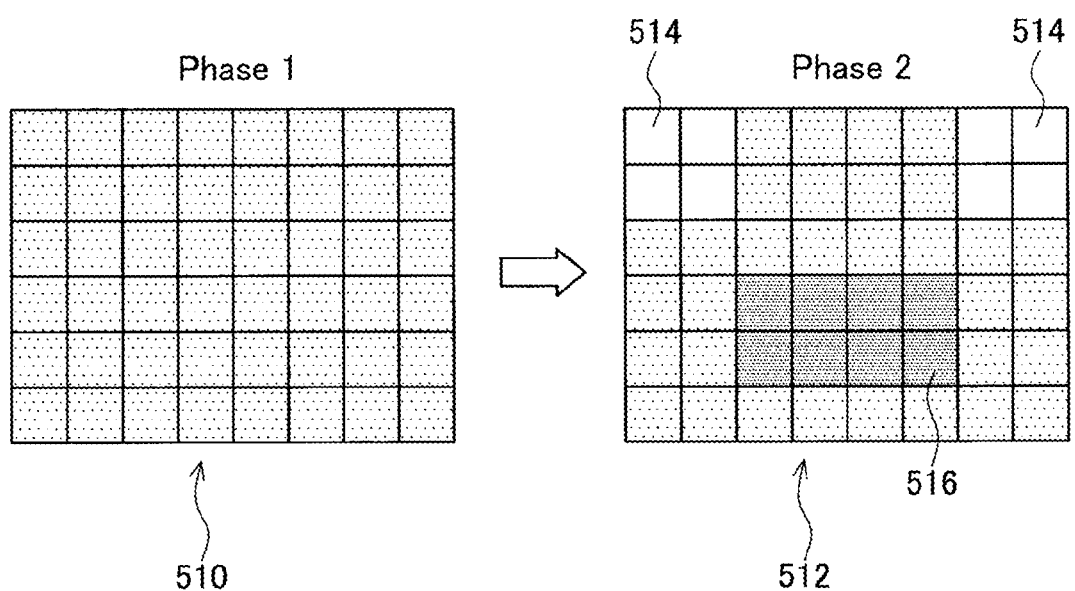
FIG. 22 is an explanatory diagram for explaining an operation example of an authentication device 10 according to a second embodiment of the present disclosure.

Therefore, in a second embodiment of the present disclosure described below, the quality of an imaged image of a fingerprint pattern obtained in first imaging is confirmed, a portion having insufficient brightness is extracted, and an irradiation pattern to be used in next imaging is selected according to an extraction result. In this way, a higher-quality fingerprint pattern image can be obtained. Details of the second embodiment will be described with reference to FIG. 22. FIG. 22 is an explanatory diagram for explaining an operation example of an authentication device 10 according to the present embodiment.

Specifically, in the present embodiment, for example, as illustrated in the left part (Phase 1) of FIG. 22, in first imaging, an irradiation pattern 510 that uniformly irradiates an entire placement surface 90 on which a fingertip 600 is placed with light by a plurality of transparent organic EL elements 100a disposed in a matrix is used. In addition, an authentication device 10 analyzes an imaged image of a fingerprint pattern obtained using the irradiation pattern 510, and extracts, for example, a high brightness region and a low brightness region.

Next, the authentication device 10 dynamically adjusts lighting or brightness of the plurality of transparent organic EL elements 100a disposed in a matrix, on the basis of an extraction result. For example, in a case where an image with high brightness in a center region is obtained, the authentication device 10 performs adjustment so as to decrease the brightness of the transparent organic EL element 100a in a center region 516 as illustrated in the right part (Phase 2) of FIG. 22. Further, for example, in a case where an image with low brightness in an end region is obtained, the authentication device 10 performs adjustment to increase the brightness of the transparent organic EL element 100a in an end region 514 as illustrated in the right part (Phase 2) of FIG. 22. Then, by performing next imaging using an irradiation pattern 512, a higher-quality fingerprint pattern image can be obtained.

Note that the present embodiment is not limited to the adjustment of the brightness, and the authentication device 10 may select a combination of the transparent organic EL elements 100a to be turned on, that is, an irradiation pattern. According to the present embodiment, with the above configuration, it is possible to suppress an increase in power consumed by a display unit 100 by performing a plurality of imaging while acquiring a fingerprint pattern of a more necessary portion.

4. Third Embodiment

<4.1 Detailed Configuration Around Fingerprint Sensor Unit 104>

Figure 23:
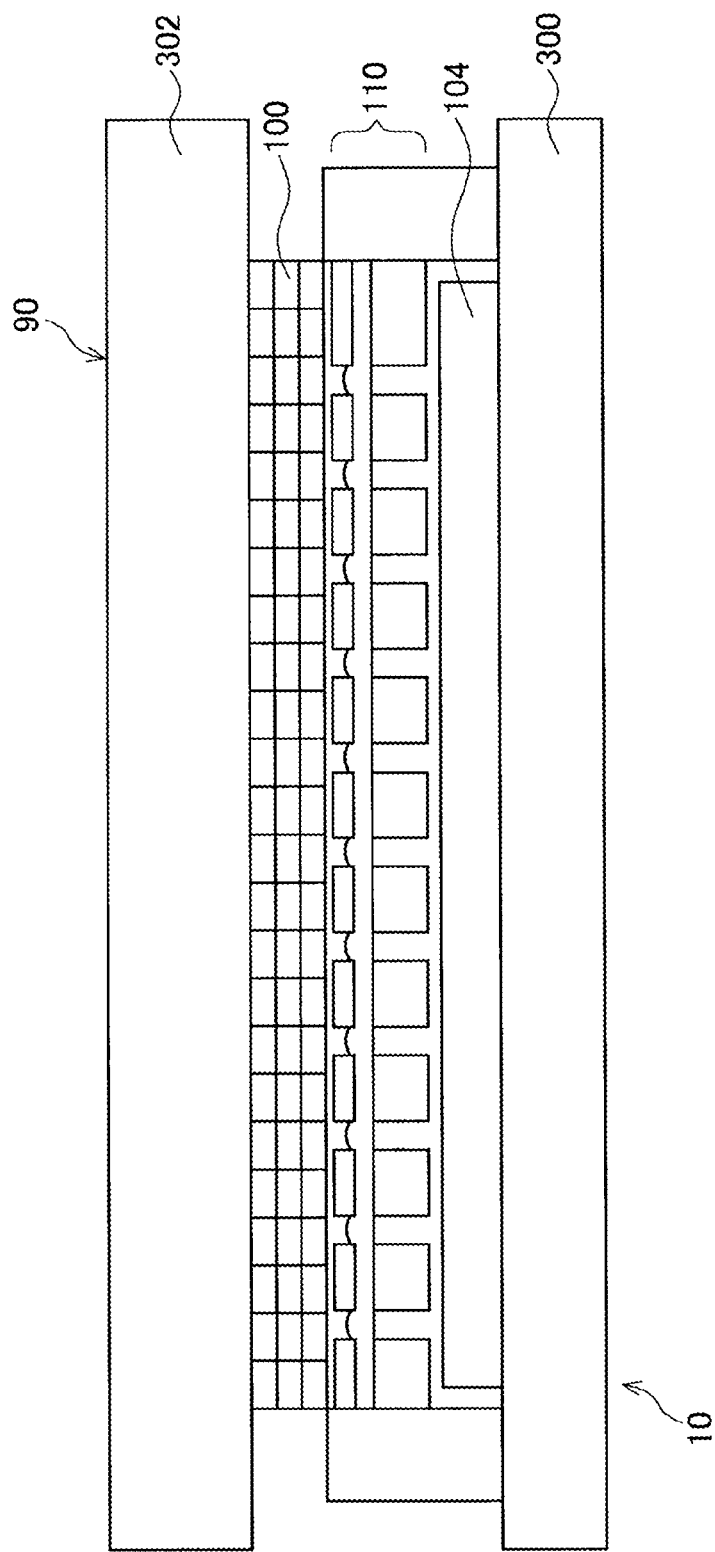
FIG. 23 is an (first) explanatory diagram for explaining a configuration example of a part of an authentication device 10 according to a third embodiment of the present disclosure.
Figure 24:
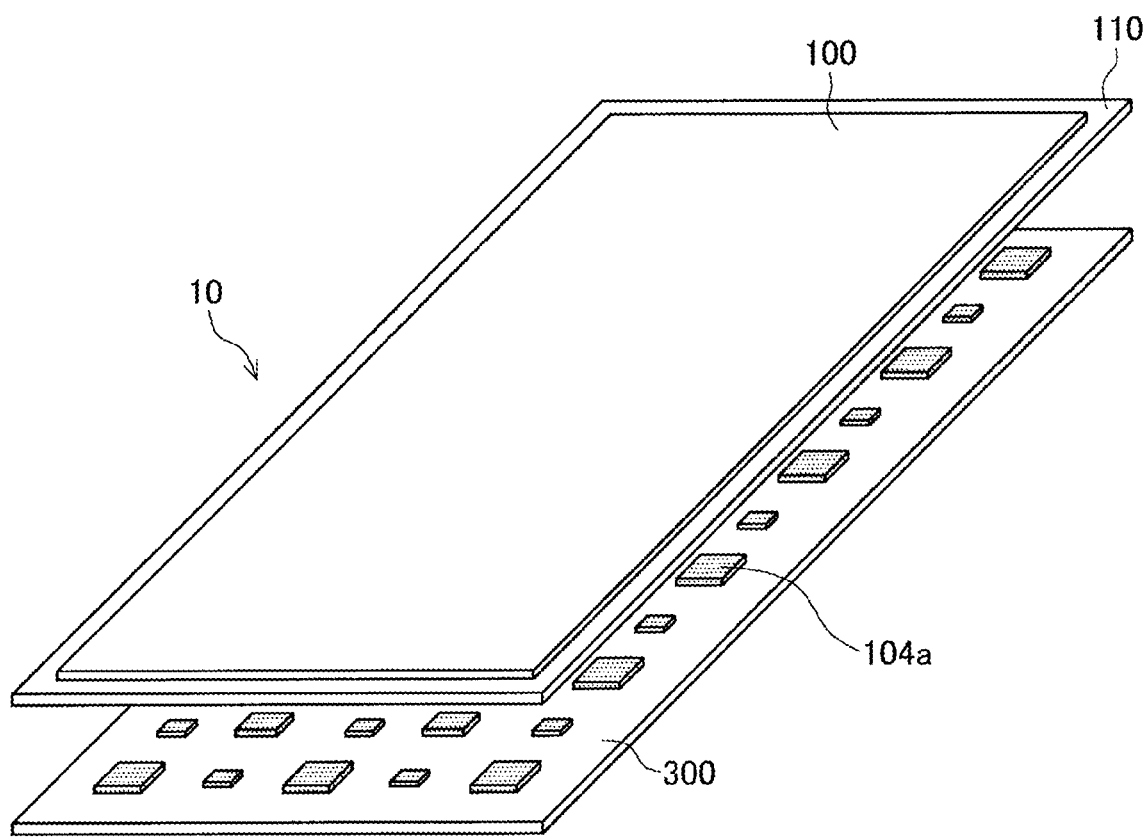
FIG. 24 is an (second) explanatory diagram for explaining a configuration example of a part of the authentication device 10 according to the third embodiment.

Furthermore, an example of a specific configuration around a fingerprint sensor unit 104 of an authentication device 10 according to the present embodiment will be described with reference to FIGS. 23 and 24. FIGS. 23 and 24 are explanatory diagrams for explaining a configuration example of a part of the authentication device 10 according to the present embodiment. Specifically, FIG. 23 illustrates a cross section of the authentication device 10 cut along a stacking direction, and FIG. 24 is an exploded perspective view schematically illustrating the authentication device 10 disassembled for each layer. Note that, in FIG. 24, illustration of a glass 302 (see FIG. 23) is omitted.

As illustrated in FIG. 23, the glass 302 is provided on an outermost surface (uppermost surface in the drawing) of the authentication device 10 according to the present embodiment in order to function as a placement surface 90 on which a fingertip 600 of a user is placed and to protect a display unit 100. Further, in the authentication device 10, the display unit 100 in which a plurality of transparent organic EL elements (light emitting elements) 100a are arranged is provided below the glass 302. In addition, the fingerprint sensor unit 104 including a plurality of imaging elements 104a arranged on a substrate 300 is provided below the display unit 100. Furthermore, a lens unit 110 made of an MLA that guides light to each imaging element 104a is provided between the display unit 100 and the fingerprint sensor unit 104. When the authentication device 10 is viewed from above the placement surface 90, in a configuration around the fingerprint sensor unit 104, as illustrated in FIG. 24, the plurality of imaging elements 104a are disposed in a matrix on the substrate 300 provided below. Further, in the authentication device 10, the lens unit 110 and the display unit 100 are stacked on each imaging element 104a. That is, in the authentication device 10 illustrated in FIGS. 23 and 24, it can be said that the display unit 100 is located on the side of the placement surface 90.

<4.2 Modification>

Figure 25:
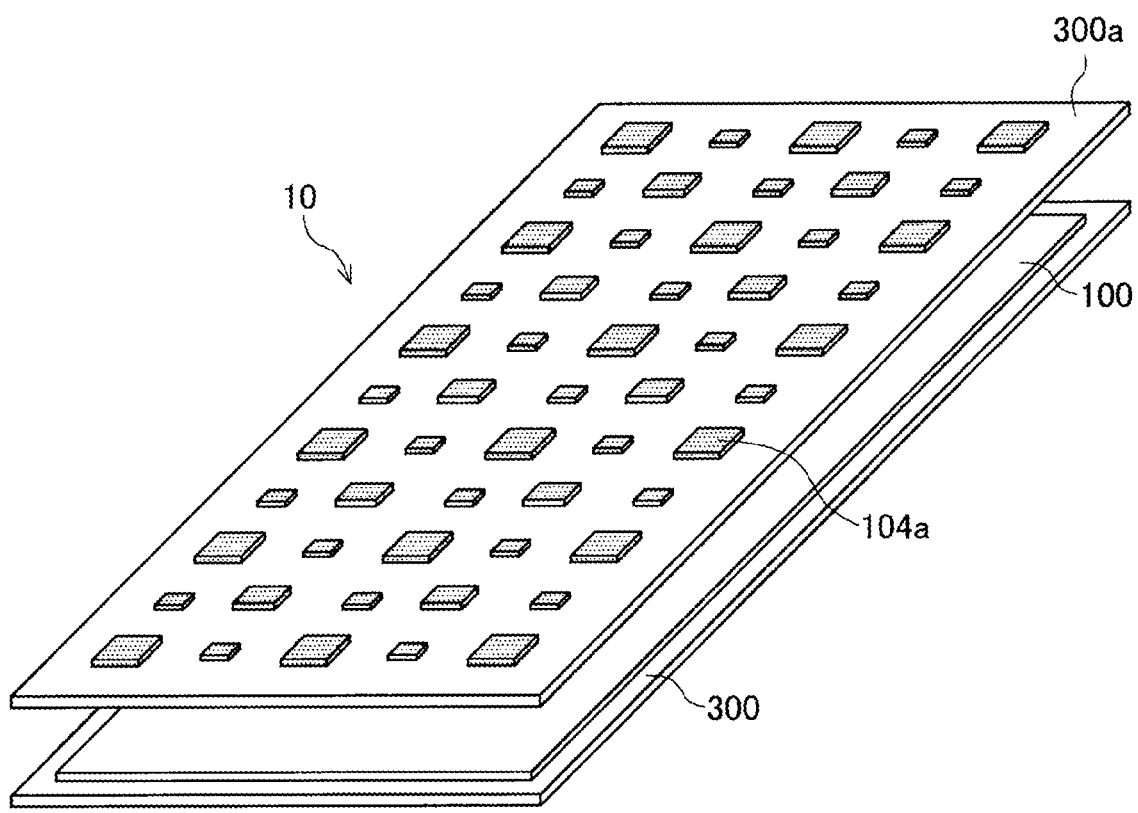
FIG. 25 is an (first) explanatory diagram for explaining a configuration example of a part of an authentication device 10 according to a modification of the third embodiment.
Figure 26:
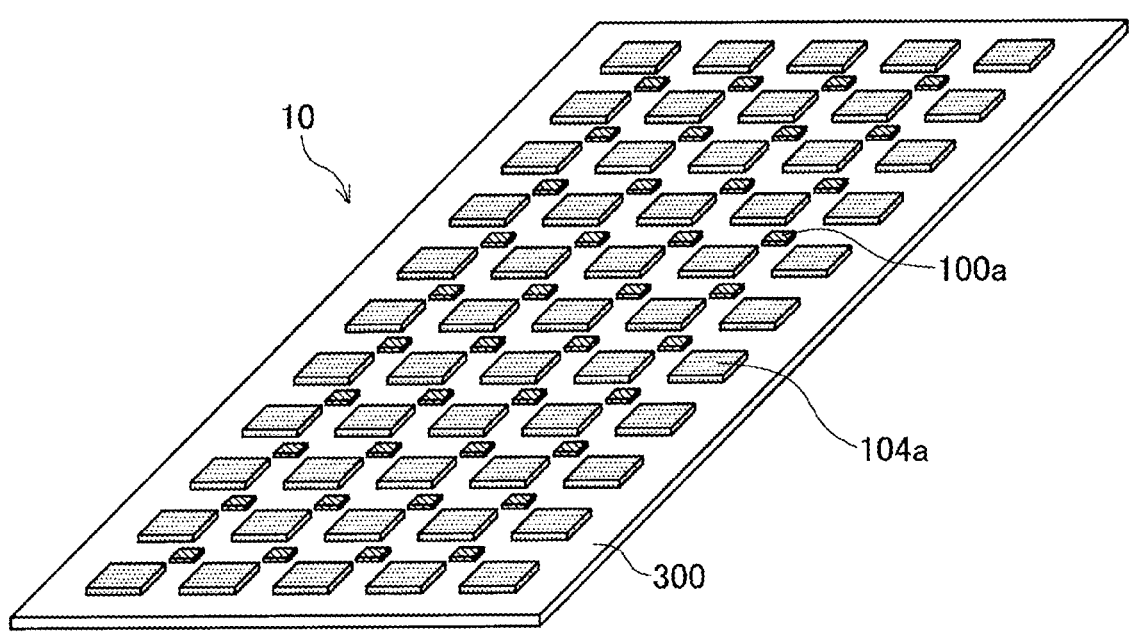
FIG. 26 is an (second) explanatory diagram for explaining a configuration example of a part of an authentication device 10 according to a modification of the third embodiment.

Further, in the present embodiment, the authentication device 10 is not limited to the form in which the display unit 100 is located on the side of the placement surface 90, and the display unit 100 may be located below the fingerprint sensor unit 104, or the display unit 100 and the fingerprint sensor unit 104 may be provided on the same surface. Therefore, an authentication device 10 according to a modification of the present embodiment will be described with reference to FIGS. 25 and 26. FIGS. 25 and 26 are explanatory diagrams for explaining a configuration example of a part of the authentication device 10 according to the modification of the present embodiment. Specifically, FIG. 25 is an exploded perspective view schematically illustrating the authentication device 10 according to the present modification disassembled for each layer, and illustration of the glass 302 is omitted in FIG. 25. FIG. 26 is a perspective view of the substrate 300 of the authentication device 10 according to the present modification.

For example, as illustrated in FIG. 25, in the authentication device 10 according to the modification, when viewed from above the placement surface 90, each imaging element 104a of the fingerprint sensor unit 104 may be provided on a transparent substrate 300a provided above the display unit 100. That is, in the authentication device 10 illustrated in FIG. 25, the fingerprint sensor unit 104 is provided above the display unit (irradiation unit) 100 so as to overlap with the display unit 100. In the present modification, since the display unit 100 and each imaging element 104a of the fingerprint sensor unit 104 can be provided in a stacked manner, the authentication device 10 can be downsized.

Further, for example, as illustrated in FIG. 26, in the authentication device 10 according to the modification, when viewed from above the placement surface 90, each transparent organic EL element 100a of the display unit 100 and each imaging element 104a of the fingerprint sensor unit 104 may be disposed on the substrate 300. Note that, in FIG. 26, illustration of the glass 302 on the outermost surface and the lens unit 110 located below the glass 302 is omitted. In the present modification, since each transparent organic EL element 100a of the display unit 100 and each imaging element 104a of the fingerprint sensor unit 104 can be provided on the same substrate 300, the authentication device 10 can be downsized.

Note that the authentication device 10 illustrated in FIGS. 25 and 26 can be operated similarly to the first embodiment described above. Specifically, the authentication device 10 according to the present modification turns on the plurality of transparent organic EL elements 100a at the predetermined positions among the plurality of transparent organic EL elements 100a, and causes the plurality of remaining transparent organic EL elements 100a that are not turned on to transmit light. Then, the authentication device 10 can image a part of the fingerprint pattern by driving a plurality of imaging elements 104a (located in the vicinity of and overlapping with the plurality of transparent organic EL elements 100a) corresponding to the plurality of transparent organic EL elements 100a that are not turned on.

5. Fourth Embodiment

Figure 27:
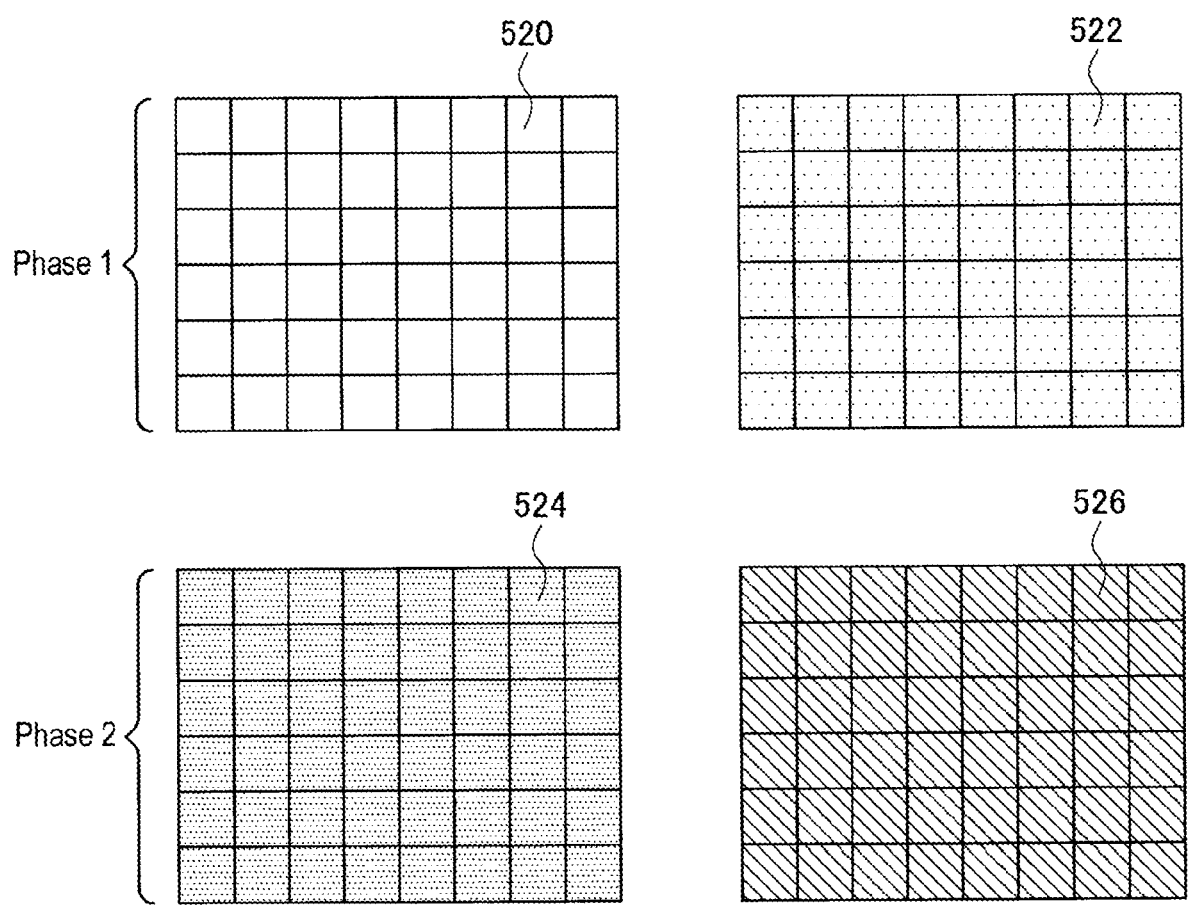
FIG. 27 is an explanatory diagram for explaining an operation example of an authentication device 10 according to a fourth embodiment of the present disclosure.

Further, an authentication device 10 according to an embodiment of the present disclosure may acquire an image of a pattern appearing on a fingertip 600 other than a fingerprint pattern by controlling a wavelength of light to be emitted. For example, the authentication device 10 may acquire a vein pattern of the fingertip 600 of the user. Therefore, as a fourth embodiment of the present disclosure, an example of acquiring the vein pattern and the like will be described with reference to FIG. 27. FIG. 27 is an explanatory diagram for explaining an operation example of the authentication device 10 according to the present embodiment.

For example, in the present embodiment, as illustrated in FIG. 27, the authentication device 10 performs imaging using an irradiation pattern 520 for emitting near infrared light and an irradiation pattern 522 for emitting infrared light as Phase 1. Next, as illustrated in FIG. 27, the authentication device 10 performs imaging using an irradiation pattern 524 for emitting green light and an irradiation pattern 526 for emitting blue light as Phase 2. That is, in the present embodiment, the authentication device 10 performs control so that a plurality of transparent organic EL elements 100a sequentially emit near infrared light, red light, green light, and blue light.

Specifically, since the near infrared light or the infrared light is easily absorbed by hemoglobin in blood in the vein, the vein appears as a shadow in an imaged image when the fingertip 600 irradiated with the near infrared light or the infrared light is imaged. Therefore, the authentication device 10 can acquire the shadow as a vein pattern by irradiating the fingertip 600 with the near infrared light or the infrared light. In the present embodiment, personal authentication can also be performed using the vein pattern acquired as described above. Further, for example, since the green light or the blue light has low transparency to body tissue, a fingerprint pattern or a sweat gland pattern of the surface of the fingertip 600 can be acquired when the fingertip 600 irradiated with the green light or the blue light is imaged. Therefore, by irradiating the fingertip 600 with the green light or the blue light, the authentication device 10 can acquire a fingerprint pattern or a sweat gland pattern of the surface of the fingertip 600, and can perform personal authentication using the pattern.

That is, in the present embodiment, by controlling the wavelength of the light with which the fingertip 600 is irradiated, the depth to which the light reaches on the surface of the fingertip 600 can be changed, so that not only the fingerprint pattern but also the vein pattern and the like can be acquired. Therefore, in the present embodiment, since two authentication methods can be used by using two different patterns appearing on the fingertip 600, personal authentication with higher security can be performed.

Further, in the present embodiment, for example, by emitting the near infrared light or the infrared light, a time-series change in the volume of the blood vessel (time-series change in blood flow) can be captured, so that it is also possible to detect a pulse or the like. Therefore, in the present embodiment, since it is also possible to determine whether or not an imaged image is obtained from a living body by detecting a time-series change in the pattern of the blood vessel, it is also possible to detect forgery for breaking the authentication. That is, according to the present embodiment, the authentication device 10 can be provided with a determination unit that determines whether or not the imaged image is obtained from the living body.

Note that, in the present embodiment, the light is not limited to the near infrared light, the red light, the green light, and the blue light, and light in other wavelength bands may be used. Further, in the present embodiment, not only information regarding the blood flow but also biometric information such as an alcohol concentration or a blood glucose level in the blood vessel may be acquired by using light in other wavelength bands. In such a case, the authentication device 10 according to the present embodiment can also function as a device for performing personal authentication for ensuring privacy when biometric information is acquired.

6. Fifth Embodiment

Figure 28:
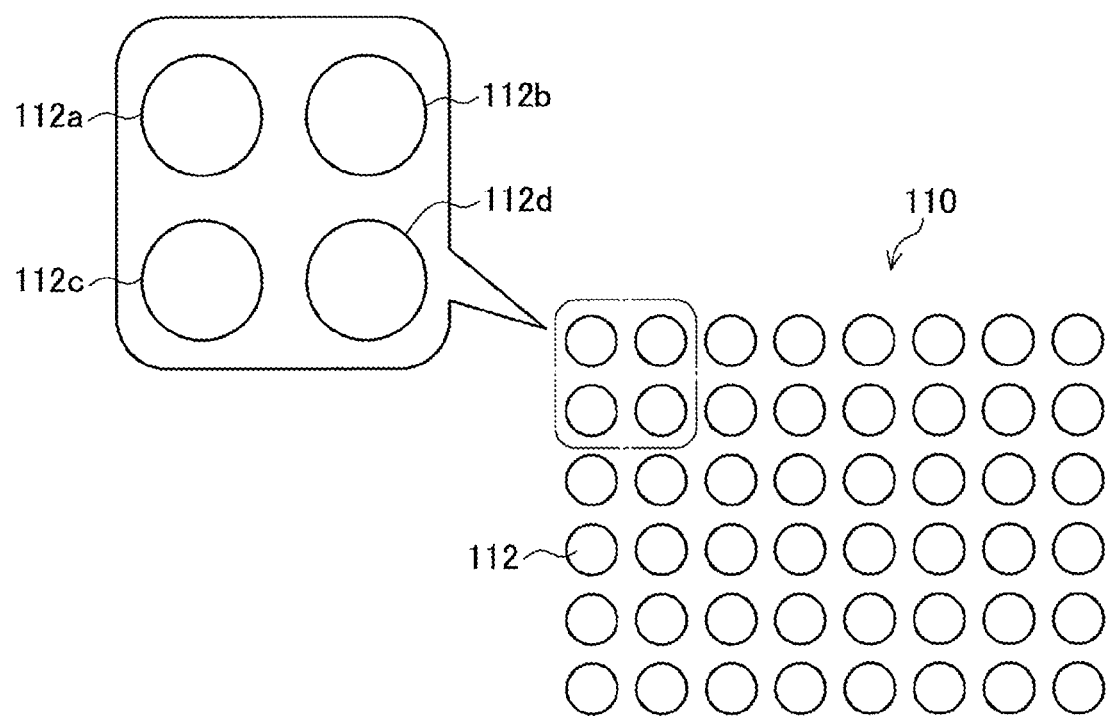
FIG. 28 is an explanatory diagram for explaining a configuration example of a part of an authentication device 10 according to a fifth embodiment of the present disclosure.

Meanwhile, in the authentication device 10 according to each of the embodiments described above, since focal distances of the lens unit 110, that is, a plurality of lenses forming a microlens array are the same, it may be difficult to acquire detailed information of unevenness of a ridge of a fingerprint pattern, and it may be difficult to extract a high-dimensional feature amount. Therefore, as a fifth embodiment of the present disclosure, an authentication device 10 using a microlens array including a plurality of lenses having different focal distances will be described with reference to FIGS. 28, 29A, 29B, 29C, and 29D. FIG. 28 is an explanatory diagram for explaining a configuration example of a part of the authentication device 10 according to the present embodiment, and FIGS. 29A, 29B, 29C and 29D are explanatory diagrams for explaining an operation example of the authentication device 10 according to the present embodiment.

Specifically, as illustrated in FIG. 28, in the present embodiment, a lens unit 110 has a microlens array including a plurality of lenses 112 disposed in a matrix. In the microlens, it is assumed that four lenses 112 arranged in a square shape have focal distances different from each other. In other words, lenses 112a, 112b, 112c, and 112d illustrated in FIG. 28 have focal distances different from each other. Therefore, these lenses 112a, 112b, 112c, and 112d can connect images of fingerprint patterns at different depths on the corresponding imaging elements 104a. Note that, in the present embodiment, the four lenses 112 arranged in a square shape are not limited to having focal distances different from each other, and for example, if at least some of the plurality of lenses 112 have focal distances different from each other, the type of focal distance can be properly selected.

In the present embodiment, in a case where the lens 112 and a transparent organic EL element 100a of a display unit 100 correspond to each other on a one-to-one basis, the authentication device 10 alternately turns on and turns off each light emitting element array, for example. However, the authentication device 10 performs control so as to form an irradiation pattern in which each transparent organic EL element 100a is alternately turned on and turned off in one light emitting element array to be turned on. More specifically, the authentication device 10 performs control to form an irradiation pattern illustrated in FIG. 29A in first imaging, and performs control to form an irradiation pattern illustrated in FIG. 29B in second imaging. Then, the authentication device 10 performs control to form an irradiation pattern illustrated in FIG. 29C in third imaging, and performs control to form an irradiation pattern illustrated in FIG. 29D in fourth imaging. In such a case, the authentication device 10 can combine imaged images 500 obtained by the four imaging to obtain a combined image 502 of the fingerprint pattern including the detailed information of the unevenness of the ridge (the information of the fingerprint pattern at the different depth).

As described above, in the present embodiment, since the detailed information of the unevenness of the ridge can be acquired, it is possible to extract a higher-dimensional feature amount, and as a result, the accuracy of authentication can be further improved. Note that, in the present embodiment, the focal distance of the lens 112 is not limited to being selected according to the unevenness of the surface of the fingertip 600, and for example, a vein of the fingertip 600, a capillary blood vessel in the dermis, and the like may be imaged by selecting the focal distance according to the inside of the fingertip 600.

7. Sixth Embodiment

In the authentication device 10 according to the fifth embodiment described above, in order to avoid images formed by a plurality of lenses 112 on imaging elements 104a from interfering with each other, a distance between the lenses 112 when viewed from above a placement surface 90 may be required to be a predetermined distance or more. In such a case, not only an area of a lens unit 110 is increased, but also areas of a display unit 100 and a fingerprint sensor unit 104 are increased accordingly, so that it may be difficult to reduce a size and a manufacturing cost of the authentication device 10. Therefore, as a sixth embodiment of the present disclosure, an authentication device 10 provided with a shutter layer 304 will be described with reference to FIG. 30. FIG. 30 is an explanatory diagram for explaining a configuration example of a part of the authentication device 10 according to the present embodiment.

Specifically, in the authentication device 10 according to the present embodiment, as illustrated in FIG. 30, the shutter layer 304 is provided between the display unit 100 and the lens unit 110. The shutter layer 304 has a plurality of shutter elements 304a made of liquid crystal and disposed in a matrix, and the shutter elements 304a are provided so as to correspond to the respective lenses 112.

The shutter element 304a includes, for example, a passive reflective liquid crystal, two transparent electrodes sandwiching the reflective liquid crystal from both sides, and two polarizing plates sandwiching the two transparent electrodes (polarization angles of the two polarizing plates are orthogonal to each other, for example). In the present embodiment, transmission and non-transmission of light can be controlled by applying a predetermined voltage between the transparent electrodes to change a structure of liquid crystal molecules and change a polarization direction of the light, so that it is possible to cause the shutter element 304a to function as a shutter. Therefore, in the present embodiment, by controlling the shutter element 304a, control is performed such that light passes only through the lens 112 having a specific focal distance, for example, only the shutter element 304a on the lens 112 having the specific focal distance transmits light. As a result, in the present embodiment, it is possible to avoid the images formed by the plurality of lenses 112 on the respective imaging elements 104a from interfering with each other, and a clear imaged image with less interference can be obtained.

As described above, in the present embodiment, since the images formed by the plurality of lenses 112 on the respective imaging elements 104a can be avoided from interfering with each other, the distance between the lenses 112 does not have to be the predetermined distance or more. Therefore, according to the present embodiment, it is possible to avoid an increase in the area of the lens unit 110 and an increase in the areas of the display unit 100 and the fingerprint sensor unit 104, and as a result, it is possible to reduce the size and the manufacturing cost of the authentication device 10. Note that, in the present embodiment, the shutter layer 304 is not limited to being provided between the display unit 100 and the lens unit 110, and for example, the shutter layer 304 may be provided between the lens unit 110 and the fingerprint sensor unit 104.

Furthermore, in the present embodiment, each lens 112 may be replaced with a lens group including a combination of a plurality of concave lenses, convex lenses, and the like, and a light shielding body provided with a pinhole. In this case, since each lens group configures, for example, a Kepler-type optical system and forms an image on one corresponding imaging element 104a, it is possible to avoid images from interfering with each other.

8. Seventh Embodiment

In the authentication device 10 according to the sixth embodiment described above, close-up shooting of a fingerprint pattern or the like can be performed. However, since it is difficult to image a subject far away from the authentication device 10, it is required to provide another imaging apparatus capable of such imaging. More specifically, in a case where the authentication device 10 according to the sixth embodiment is provided in a smartphone or the like, since it is difficult for the authentication device 10 to perform a function of imaging a subject (person or landscape) away from the smartphone, another imaging apparatus may be provided in the smartphone. For this reason, it may be difficult to reduce a size and a manufacturing cost of the smartphone.

Figure 31:
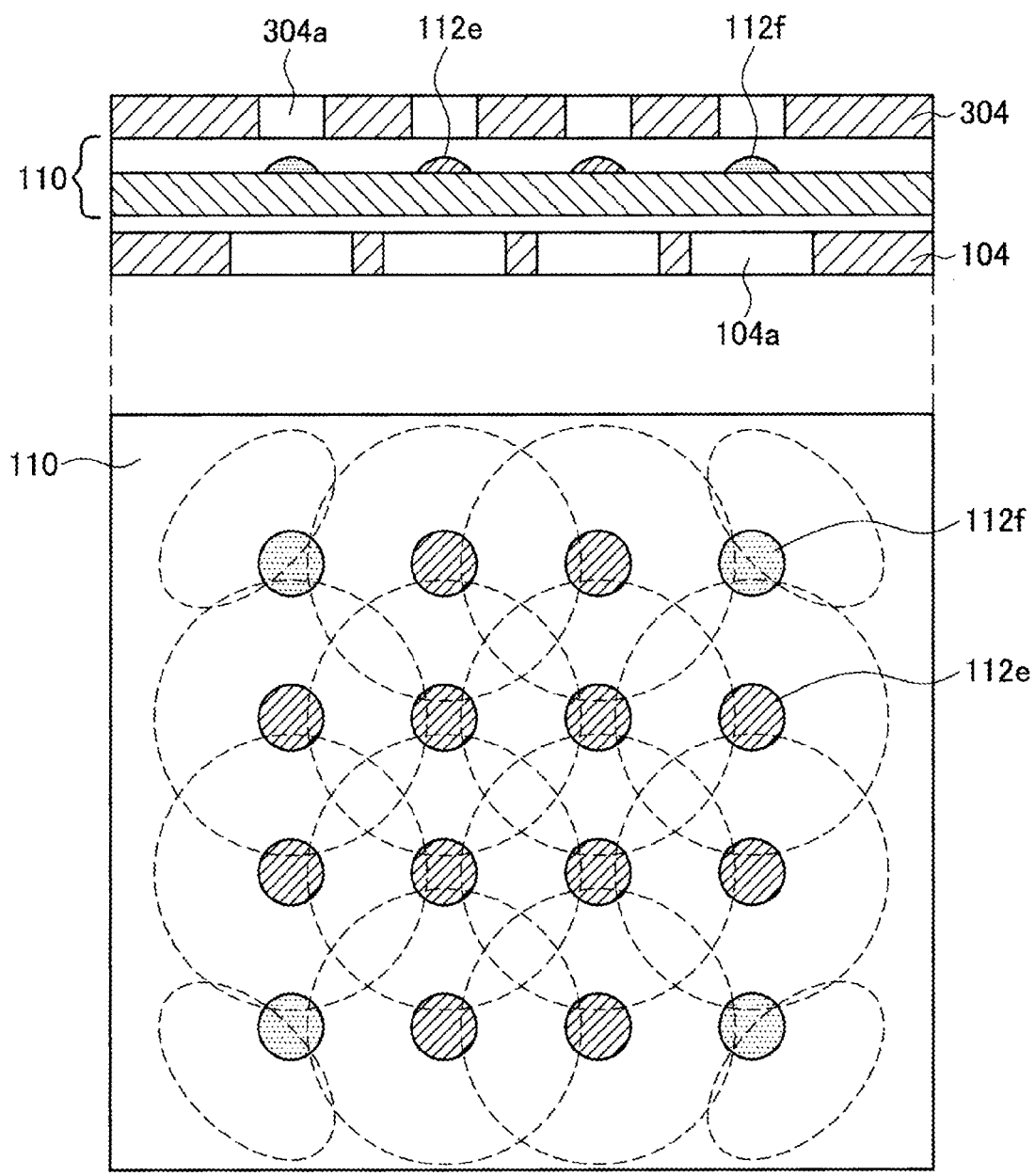
FIG. 31 is an explanatory diagram for explaining a configuration example of a part of an authentication device 10 according to a seventh embodiment of the present disclosure.
Figure 32:
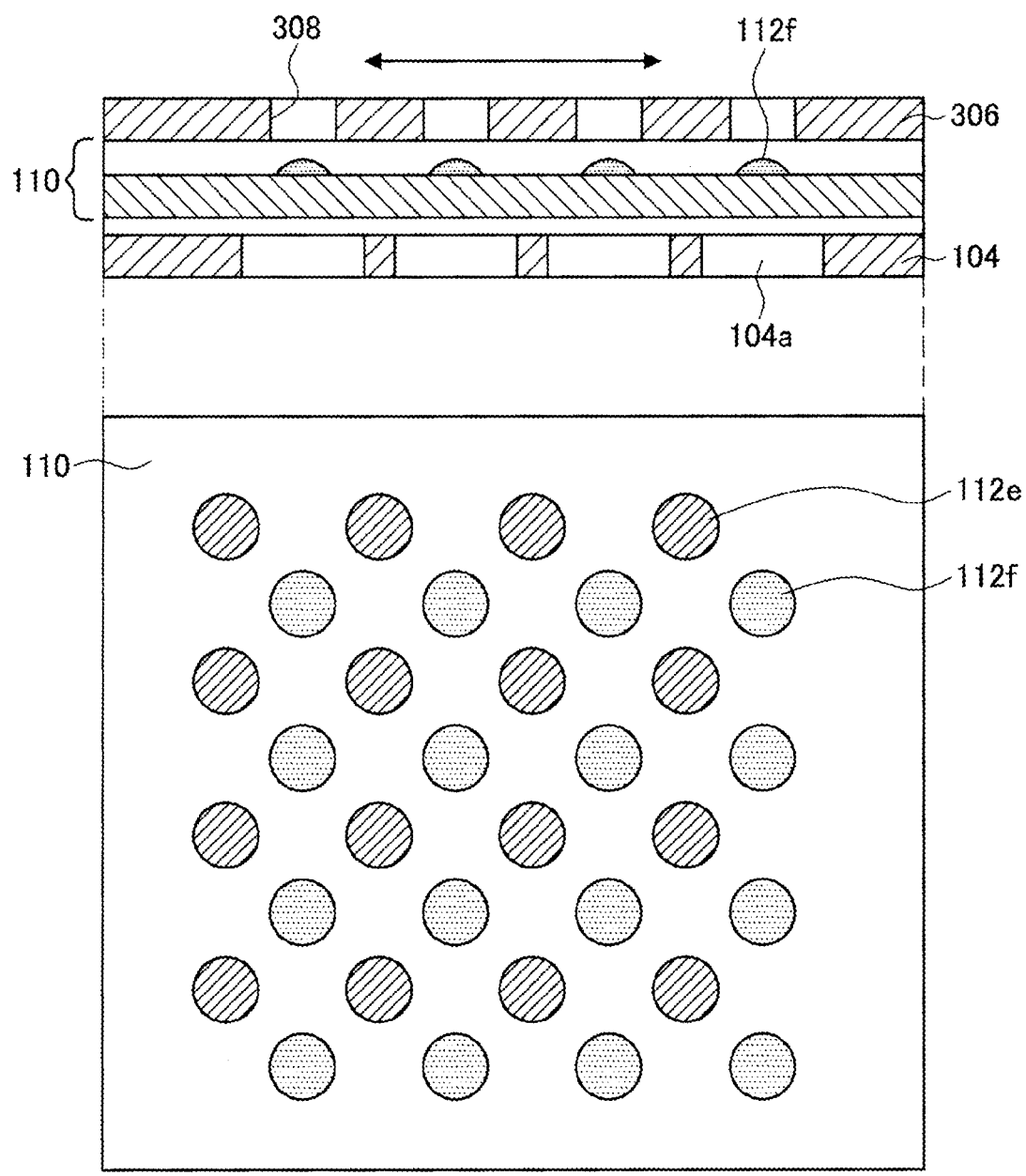
FIG. 32 is an explanatory diagram for explaining a configuration example of a part of an authentication device 10 according to a modification of the seventh embodiment.
Figure 33:
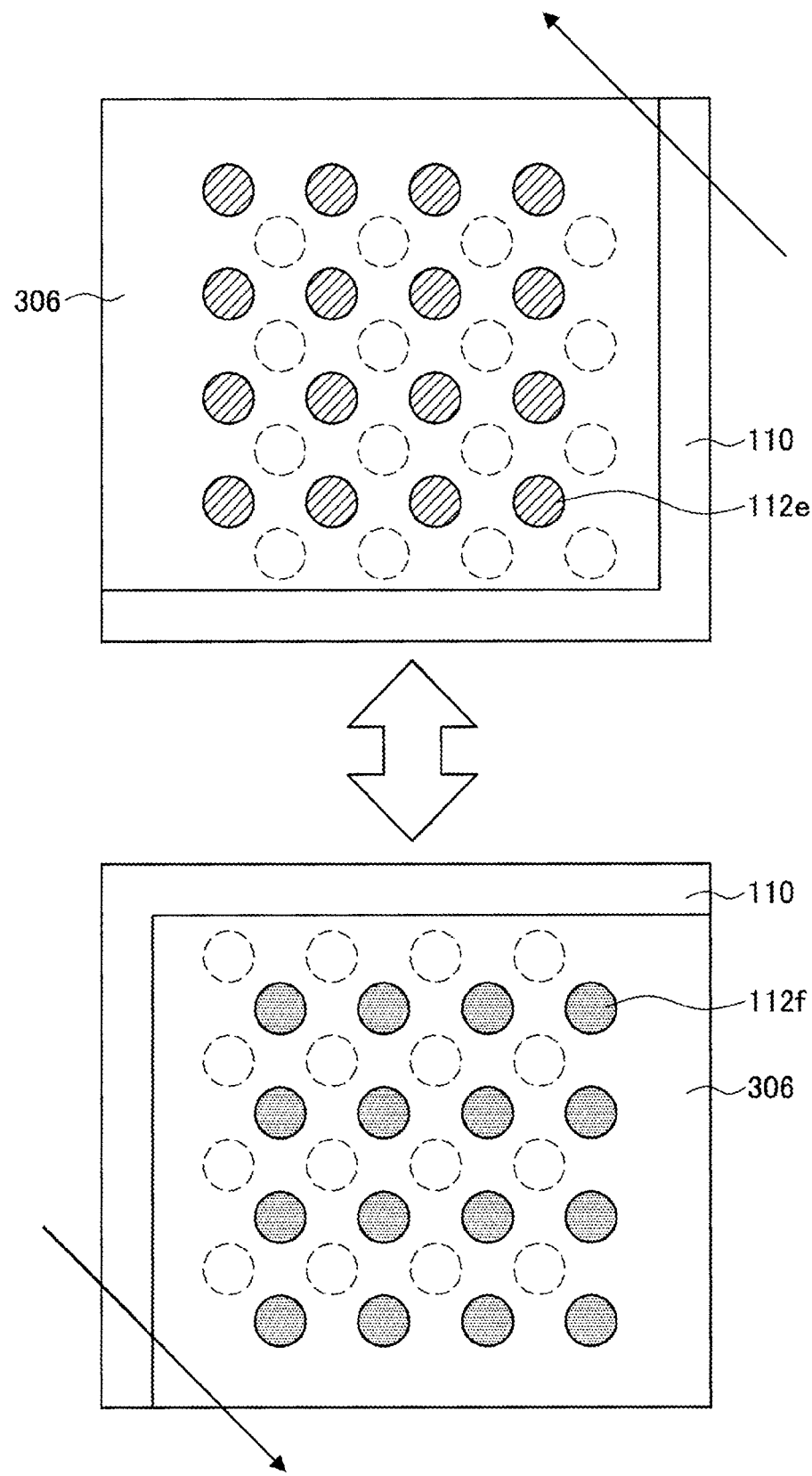
FIG. 33 is an explanatory diagram for explaining an operation example of the authentication device 10 according to the seventh embodiment.

Therefore, as a seventh embodiment of the present disclosure, an authentication device 10 capable of imaging a distant subject will be described with reference to FIGS. 31 and 32. FIG. 31 is an explanatory diagram for explaining a configuration example of a part of the authentication device 10 according to the present embodiment, in which an upper part is a cross-sectional view of the authentication device 10 and a lower part is a plan view of a lens unit 110 of the authentication device 10. Further, FIG. 32 is an explanatory diagram for explaining a configuration example of a part of an authentication device 10 according to a modification of the present embodiment, in which an upper part is a cross-sectional view of the authentication device 10 and a lower part is a plan view of the lens unit 110 of the authentication device 10. Further, FIG. 33 is an explanatory diagram for explaining an operation example of the authentication device 10 according to the present embodiment.

Specifically, in the present embodiment, as illustrated in the upper part of FIG. 31, a shutter layer 304 is provided above the lens unit 110, similarly to the sixth embodiment described above. The shutter layer 304 has a plurality of shutter elements 304a disposed in a matrix, and the shutter elements 304a are provided so as to correspond to respective lenses 112. Further, in the present embodiment, as illustrated in the lower part of FIG. 31, the lens unit 110 has a plurality of lenses 112 disposed in a matrix, and these lenses 112 include close-up lenses 112e and lenses 112f for imaging a distant subject. In the present embodiment, since the close-up lens 112e and the lens 112f for imaging the distant subject are included, the authentication device 10 can perform a function of imaging not only the fingerprint pattern but also the distant subject. Note that, in the example of FIG. 31, since the lens 112f is disposed at the corner of the lens unit 110, it is difficult to perform close-up shooting at the corner of the lens unit 110, but it is preferable to perform designing so as to cover an image in the case of close-up shooting by the lens 112e adjacent to the lens 112f.

As described above, in the present embodiment, since the authentication device 10 can perform the function of imaging not only the fingerprint pattern but also the distant subject, it is possible to reduce the size and the manufacturing cost of the smartphone even in a case where the authentication device 10 is provided in the smartphone or the like. For example, the authentication device 10 can image not only the fingerprint pattern but also a face of a user in order to perform face authentication, or can image a one-dimensional code (for example, a bar code or the like) and a two-dimensional code (for example, a QR code (registered trademark) or the like).

Further, as a modification of the present embodiment, a light shielding plate 306 having an opening 308 may be provided instead of the shutter layer 304. Specifically, as illustrated in the upper part of FIG. 32, the light shielding plate 306 having the opening 308 is provided above the lens unit 110. In the present modification, the opening 308 is provided so that a position thereof corresponds to a position of the close-up lens 112e of the lens unit 110 and a position of the lens 112f for imaging the distant subject.

In the present modification, as illustrated in FIG. 33, the light shielding plate 306 is mechanically moved by an actuator formed by micro electro mechanical systems (MEMS) to switch a position where light enters the lens unit 110 via the opening 308. In the present modification, for example, as illustrated in the upper part of FIG. 33, it is possible to cause the light to enter only the lens 112e by moving the light shielding plate 306, and as illustrated in the lower part of FIG. 33, it is possible to cause the light to enter only the lens 112f by moving the light shielding plate 306. Therefore, even in the present modification, the authentication device 10 can perform a function of imaging not only the fingerprint pattern but also the distant subject. Note that the present modification is not limited to mechanically moving the light shielding plate 306 so as to select a lens with a different focal point, and for example, the light shielding plate 306 may be mechanically moved so as to select a lens with a different angle of view. Further, in the present modification, the light shielding plate 306 is not limited to being provided above the lens unit 110, and for example, the light shielding plate 306 may be provided between the lens unit 110 and the fingerprint sensor unit 104.

9. Application

The authentication device 10 according to each embodiment of the present disclosure described above can be used to ensure security of personal information such as biometric information and asset information, electronic payment, and the like. Further, the authentication device 10 according to the present embodiment can also be applied to a security device installed at a gate of a facility or a door of an automobile, and a security device installed in an IoT device. Further, the authentication device 10 according to the present embodiment may be applied to a medical device (a device for managing medicines and supplements to be dispensed to each individual, a device for managing surgery to be performed to each individual, and the like) not only for ensuring security but also for ensuring safety. In addition, the authentication device 10 according to each embodiment of the present disclosure can also be an imaging apparatus that simply images a fingerprint pattern or the like.

10. Summary

As described above, according to each embodiment of the present disclosure, it is possible to provide the authentication device 10 that can be downsized and can acquire a high-quality imaged image such as a fingerprint pattern.

11. Hardware Configuration

Figure 34:
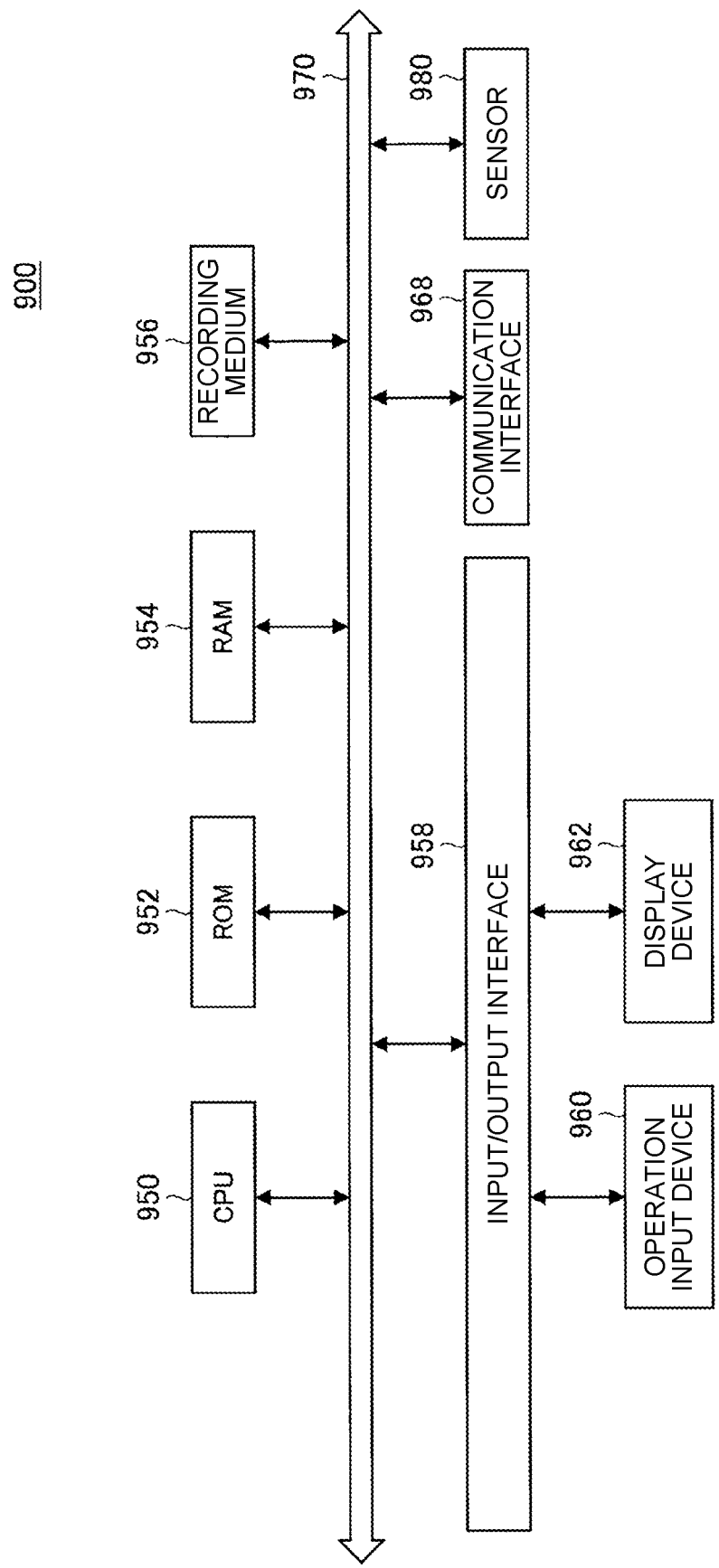
FIG. 34 is an explanatory diagram illustrating an example of a hardware configuration of an information processing apparatus 900 according to an embodiment of the present disclosure.

FIG. 34 is an explanatory diagram illustrating an example of a hardware configuration of an information processing apparatus 900 according to the present embodiment. In FIG. 34, the information processing apparatus 900 illustrates an example of a hardware configuration of the authentication device 10 described above.

The information processing apparatus 900 has, for example, a CPU 950, a ROM 952, a RAM 954, a recording medium 956, an input/output interface 958, and an operation input device 960. The information processing apparatus 900 further has a display device 962, a communication interface 968, and a sensor 980. Further, the information processing apparatus 900 connects the respective components by, for example, a bus 970 as a data transmission path.

(CPU 950)

The CPU 950 includes, for example, one or more processors including an arithmetic circuit such as a CPU, various processing circuits, and the like, and functions as a control unit (not illustrated) that controls the entire information processing apparatus 900, or the above-described control unit 200.

(ROM 952 and RAM 954)

The ROM 952 stores programs used by the CPU 950, control data such as calculation parameters, and the like. The RAM 954 temporarily stores, for example, a program executed by the CPU 950. The ROM 952 and the RAM 954 function as, for example, the storage unit 210 described above in the information processing apparatus 900.

(Recording Medium 956)

The recording medium 956 functions as the storage unit 210 described above, and stores, for example, various data such as data related to the authentication method according to the present embodiment and various applications. Here, examples of the recording medium 956 include a magnetic recording medium such as a hard disk, and a nonvolatile memory such as a flash memory. Further, the recording medium 956 may be detachable from the information processing apparatus 900.

(Input/Output Interface 958, Operation Input Device 960, and Display Device 962)

The input/output interface 958 connects, for example, the operation input device 960, the display device 962, and the like. Examples of the input/output interface 958 include a universal serial bus (USB) terminal, a digital visual interface (DVI) terminal, a high-definition multimedia interface (HDMI) (registered trademark) terminal, various processing circuits, and the like.

The operation input device 960 functions as an operation unit (not illustrated), is provided in the information processing apparatus 900, for example, and is connected to the input/output interface 958 inside the information processing apparatus 900. Examples of the operation input device 960 include a keyboard, a button, an arrow key, a rotary selector such as a jog dial, a touch panel, or a combination thereof.

The display device 962 functions as an information presentation device including the above-described display unit 100, is provided on the information processing apparatus 900, for example, and is connected to the input/output interface 958 inside the information processing apparatus 900. Examples of the display device 962 include an organic electro-luminescence (EL) display and the like.

Note that it goes without saying that the input/output interface 958 can be connected to an external device such as an operation input device (for example, a keyboard, a mouse, or the like) outside the information processing apparatus 900 or an external display device.

(Communication Interface 968)

The communication interface 968 is a communication mechanism included in the information processing apparatus 900, and functions as a communication unit (not illustrated) for performing wireless or wired communication with an external device such as a server via a network (or directly). Here, examples of the communication interface 968 include a communication antenna and a radio frequency (RF) circuit (wireless communication), an IEEE 802.15.1 port and a transmission/reception circuit (wireless communication), an IEEE 802.11 port and a transmission/reception circuit (wireless communication), a local area network (LAN) terminal and a transmission/reception circuit (wired communication), and the like.

(Sensor 980)

The sensor 980 functions as the fingerprint sensor unit 104 and the touch sensor unit 102 described above, and is, for example, a sensor capable of detecting fingerprint information of the user and detecting contact of the fingertip 600 of the user.

Note that the hardware configuration of the information processing apparatus 900 is not limited to the configuration illustrated in FIG. 34. For example, the information processing apparatus 900 may not include the communication interface 968 in a case of communicating with an external device or the like via a connected external communication device or in a case of a configuration of performing processing in a stand-alone manner. Further, the communication interface 968 may have a configuration capable of communicating with one or more external devices by a plurality of communication methods. Further, the information processing apparatus 900 can have a configuration that does not include the recording medium 956, the operation input device 960, the display device 962, and the like, for example.

Although the information processing apparatus 900 has been described above as the present embodiment, the present embodiment is not limited to such a form. The present embodiment can also be applied to various devices capable of performing processing related to an information processing method according to the present embodiment, for example, a communication device such as a mobile phone.

Further, the information processing apparatus 900 according to the present embodiment may be applied to a system including a plurality of devices on the premise of connection to a network (or communication between devices), for example, like cloud computing. That is, the information processing apparatus 900 according to the present embodiment described above can also be realized as an information processing system that performs processing related to the information processing method according to the present embodiment by a plurality of devices, for example.

An example of the hardware configuration of the information processing apparatus 900 has been described above. Each of the above-described components may be configured using a general-purpose member, or may be configured by hardware specialized for the function of each component. Such a configuration can be properly changed according to a technical level at the time of implementation.

12. Supplement

Note that the embodiment of the present disclosure described above can include, for example, a program for causing a computer to function as the information processing apparatus according to the present embodiment, and a non-transitory tangible medium on which the program is recorded. In addition, the program may be distributed via a communication line (including wireless communication) such as the Internet.

The preferred embodiments of the present disclosure have been described in detail with reference to the accompanying drawings, but the technical scope of the present disclosure is not limited to such examples. It is obvious that a person with an ordinary skill in a technological field of the present disclosure could conceive of various alterations or corrections within the scope of the technical ideas described in the appended claims, and it should be understood that such alterations or corrections will naturally belong to the technical scope of the present disclosure.

Furthermore, the effects described in the present specification are merely illustrative or exemplary and are not restrictive. That is, the technology according to the present disclosure can exhibit other effects obvious to those skilled in the art from the description of the present specification in addition to or in place of the above effects.

Note that the following configurations also belong to the technical scope of the present disclosure.

(1) An imaging apparatus comprising:
   an irradiation unit that irradiates a subject with light;
   an imaging unit that images the subject a plurality of times;
   a control unit that controls the imaging unit and the irradiation unit; and
   a combination unit that combines a plurality of imaged images obtained by the imaging unit, wherein
   the imaging unit has a plurality of imaging elements disposed in a matrix when viewed from the side of the subject,
   the irradiation unit has a plurality of light emitting elements provided so as to correspond to the plurality of imaging elements, and
   the control unit
   controls the irradiation unit so as to turn on the plurality of light emitting elements different for each imaging among the plurality of light emitting elements, and
   controls the imaging unit so as to drive the plurality of imaging elements corresponding to the plurality of light emitting elements that are not turned on.

(2) The imaging apparatus according to (1), further comprising:
   a placement surface on which a part of a body of a user is placed, wherein
   the irradiation unit is provided below the placement surface and irradiates the part of the body placed on the placement surface with light, and
   the imaging unit is provided below the placement surface and images a pattern appearing on the part of the body placed on the placement surface a plurality of times.

(3) The imaging apparatus according to (2), wherein
   the plurality of light emitting elements are disposed in a matrix when viewed from above the placement surface.

(4) The imaging apparatus according to (3), wherein
   the imaging unit is provided below the irradiation unit so as to overlap with the irradiation unit, and
   the control unit
   controls the irradiation unit so as to transmit light with respect to the plurality of light emitting elements that are not turned on, and controls the imaging unit so as to drive the plurality of imaging elements overlapping with the plurality of light emitting elements that are not turned on when viewed from above the placement surface.
(5) The imaging apparatus according to (4), further comprising:
a microlens array unit that is provided between the irradiation unit and the imaging unit and has a plurality of microlenses disposed in a matrix when viewed from above the placement surface.
(6) The imaging apparatus according to (5), wherein at least some of the plurality of microlenses have focal distances different from each other.
(7) The imaging apparatus according to (5) or (6), further including:
a shutter layer that is provided between the irradiation unit and the microlens array unit or between the microlens array unit and the imaging unit.
(8) The imaging apparatus according to (5) or (6), further including:
a light shielding plate that is provided between the irradiation unit and the microlens array unit or between the microlens array unit and the imaging unit and has a plurality of openings; and
an actuator that moves the light shielding plate.
(9) The imaging apparatus according to any one of (2) to (8), wherein
the irradiation unit has a plurality of light emitting element arrays each including the plurality of light emitting elements arranged along a predetermined direction when viewed from above the placement surface,
the plurality of light emitting element arrays are arranged along a direction perpendicular to the predetermined direction, and
the control unit controls the irradiation unit such that the light emitting element arrays are alternately turned on and turned off for each predetermined number of the light emitting element arrays in each imaging.
(10) The imaging apparatus according to any one of (2) to (8), wherein
the control unit controls the irradiation unit such that the light emitting elements are alternately turned on and turned off in a checkered pattern when viewed from above the placement surface in each imaging.
(11) The imaging apparatus according to any one of (2) to (8), wherein
the irradiation unit has a plurality of light emitting element arrays each including the plurality of light emitting elements arranged along a predetermined direction when viewed from above the placement surface, and
the control unit controls the irradiation unit such that the plurality of light emitting elements in the light emitting element array are alternately turned on and turned off for every predetermined number when viewed from above the placement surface in each imaging.
(12) The imaging apparatus according to any one of (1) to (8), wherein
the control unit selects the plurality of light emitting elements turned on in next imaging, on the basis of the imaged image obtained in previous imaging.
(13) The imaging apparatus according to any one of (1) to (8), wherein
the control unit adjusts brightness of the plurality of light emitting elements turned on in next imaging, on the basis of the imaged image obtained in previous imaging.
(14) The imaging apparatus according to (1), wherein
the imaging unit is provided above the irradiation unit so as to overlap with the irradiation unit.
(15) The imaging apparatus according to (2), further comprising:
a substrate that is provided below the placement surface so as to overlap with the placement surface, wherein
the plurality of light emitting elements and the plurality of imaging elements are disposed on the substrate.
(16) The imaging apparatus according to any one of (2) to (8), wherein
the irradiation unit functions as a display unit that displays guidance information for guiding the user to place a part of the body of the user on the placement surface under the control of the control unit.
(17) The imaging apparatus according to any one of (1) to (16), further comprising: an authentication unit that authenticates the user on the basis of a combined image obtained by the combination unit.
(18) The imaging apparatus according to (17), wherein the authentication unit authenticates the user on the basis of feature information of a fingerprint appearing on a fingertip of the user.
(19) The imaging apparatus according to any one of (2) to (8), wherein the control unit controls the plurality of light emitting elements so as to sequentially emit near infrared light, red light, green light, and blue light.
(20) The imaging apparatus according to (19), further comprising: a determination unit that determines whether or not the imaged image has been obtained from a living body, on the basis of the imaged image.
(21) The imaging apparatus according to (20), wherein the determination unit determines whether or not the imaged image has been obtained from a living body, on the basis of a time-series change in blood flow appearing on a fingertip of the user.
(22) The imaging apparatus according to any one of (2) to (8), wherein the imaging apparatus is included in a wearable terminal worn on the body of the user or a mobile terminal used by the user.
(23) An imaging method using an imaging apparatus, the imaging apparatus including
an irradiation unit that irradiates a subject with light,
an imaging unit that images the subject a plurality of times,
a control unit that controls the imaging unit and the irradiation unit, and
a combination unit that combines a plurality of imaged images obtained by the imaging unit,
the imaging unit having a plurality of imaging elements disposed in a matrix when viewed from the side of the subject,
the irradiation unit having a plurality of light emitting elements provided so as to correspond to the plurality of imaging elements,
the imaging method comprising:
turning on the plurality of light emitting elements different for each imaging among the plurality of light emitting elements; and driving the plurality of imaging elements corresponding to the plurality of light emitting elements that are not turned on.

(24) A program for causing a computer to realize control of an imaging apparatus, the imaging apparatus including an irradiation unit that irradiates a subject with light, an imaging unit that images the subject a plurality of times, a control unit that controls the imaging unit and the irradiation unit, and a combination unit that combines a plurality of imaged images obtained by the imaging unit, the imaging unit having a plurality of imaging elements disposed in a matrix when viewed from the side of the subject, the irradiation unit having a plurality of light emitting elements provided so as to correspond to the plurality of imaging elements, wherein the program causes the computer to realize:

a function of turning on the plurality of light emitting elements different for each imaging among the plurality of light emitting elements; and a function of driving the plurality of imaging elements corresponding to the plurality of light emitting elements that are not turned on.

REFERENCE SIGNS LIST 10, 10a AUTHENTICATION DEVICE
90 PLACEMENT SURFACE
100 DISPLAY UNIT
100a TRANSPARENT ORGANIC EL ELEMENT
102 TOUCH SENSOR UNIT
104 FINGERPRINT SENSOR UNIT
104a IMAGING ELEMENT
110 LENS UNIT
112, 112a, 112b, 112c, 112d, 112e, 112f LENS
150 BAND PORTION
160 LIGHT GUIDE PLATE
162 IRRADIATION UNIT
200 CONTROL UNIT
202 IMAGING CONTROL UNIT
204 DATA COMBINATION UNIT
206 AUTHENTICATION UNIT
208 OUTPUT CONTROL UNIT
210 STORAGE UNIT
300, 300a SUBSTRATE
302 GLASS
304 SHUTTER LAYER
304a SHUTTER ELEMENT
306 LIGHT SHIELDING PLATE
308 OPENING
500a, 500b, 500c, 500d IMAGED IMAGE
502 COMBINED IMAGE
510, 512, 520, 522, 524, 526 IRRADIATION PATTERN
514 END REGION
516 CENTER REGION
600 FINGERTIP
900 INFORMATION PROCESSING APPARATUS
950 CPU
952 ROM
954 RAM
956 RECORDING MEDIUM
958 INPUT/OUTPUT INTERFACE
960 OPERATION INPUT DEVICE
962 DISPLAY DEVICE
968 COMMUNICATION INTERFACE
970 BUS
980 SENSOR

The invention claimed is:

1. An imaging apparatus, comprising:
an irradiation unit configured to irradiate a subject with light;
an imaging unit configured to image the subject a plurality of times to obtain a plurality of imaged images; and
a central processing unit (CPU) configured to:
control each of the imaging unit and the irradiation unit; and
combine the obtained plurality of imaged images, wherein
the imaging unit includes a plurality of imaging elements in a matrix,
the irradiation unit includes a plurality of light emitting elements,
each light emitting element of the plurality of light emitting elements is associated with a corresponding imaging element of the plurality of imaging elements, and
the CPU is further configured to:
control the irradiation unit to:
turn on a first set of light emitting elements of the plurality of light emitting elements; and
turn off a second set of light emitting elements of the plurality of light emitting elements, wherein the second set of light emitting elements is different from the first set of light emitting elements; and
control the imaging unit to drive a set of imaging elements of the plurality of imaging elements, wherein the set of imaging elements is associated with the second set of light emitting elements.

2. The imaging apparatus according to claim 1, further comprising a placement surface on which a part of a body of a user is placed, wherein
the irradiation unit is below the placement surface,
the irradiation unit is further configured to irradiate the part of the body placed on the placement surface with the light,
the imaging unit is below the placement surface, and
the imaging unit is further configured to image, a pattern appearing on the part of the body placed on the placement surface, the plurality of times.

3. The imaging apparatus according to claim 2, wherein the plurality of light emitting elements is in a matrix when viewed from above the placement surface.

4. The imaging apparatus according to claim 3, wherein the imaging unit is below the irradiation unit so as to overlap with the irradiation unit, and
the CPU is further configured to:
control the irradiation unit so allow light reflected from the part of the body to pass through the second set of light emitting elements of the plurality of light emitting elements; and
control the imaging unit to drive the set of imaging elements overlapping with the second set of light emitting elements when viewed from above the placement surface.

5. The imaging apparatus according to claim 4, further comprising a microlens array unit between the irradiation unit and the imaging unit, wherein the microlens array unit includes a plurality of microlenses in a matrix when viewed from above the placement surface.

6. The imaging apparatus according to claim 5, wherein a first microlens of the plurality of microlenses has a focal distance different from a focal distance of a second microlens of the plurality of microlenses.

7. The imaging apparatus according to claim 5, further comprising at least one of:
a shutter layer between the irradiation unit and the microlens array unit or between the microlens array unit and the imaging unit, or
a light shielding plate between the irradiation unit and the microlens array unit or between the microlens array unit and the imaging unit, wherein the light shielding plate includes:
a plurality of openings, and
an actuator configured to move the light shielding plate.

8. The imaging apparatus according to claim 2, further comprising a substrate below the placement surface so as to overlap with the placement surface, wherein the plurality of light emitting elements and the plurality of imaging elements are on the substrate.

9. The imaging apparatus according to claim 2, wherein the irradiation unit functions as a display unit, and
the display unit is configured to display, based on the control of the irradiation unit, guidance information for guiding the user to place the part of the body of the user on the placement surface.

10. The imaging apparatus according to claim 2, wherein the CPU is further configured to control the plurality of light emitting elements to sequentially emit each of near infrared light, red light, green light, and blue light.

11. The imaging apparatus according to claim 10, further comprising a determination unit configured to determine, based on the plurality of imaged images, whether an imaged image of the plurality of imaged images is obtained from a living body.

12. The imaging apparatus according to claim 11, wherein the determination unit is further configured to determine whether the imaged image is obtained from the living body based on a time-series change in blood flow appearing on a fingertip of the user.

13. The imaging apparatus according to claim 2, wherein the imaging apparatus is in at least one of:
a wearable terminal worn on the body of the user, or
a mobile terminal used by the user.

14. The imaging apparatus according to claim 1, wherein the CPU is further configured to:
obtain, in a first imaging operation, an imaged image of the plurality of imaged images; and
select, based on the obtained imaged image, the first set of light emitting elements to be turned on in a second imaging operation that is subsequent to the first imaging operation.

15. The imaging apparatus according to claim 1, wherein the CPU is further configured to:
obtain, in a first imaging operation, an imaged image of the plurality of imaged images; and
adjust, based on the obtained imaged image, brightness of the first set of light emitting elements in a second imaging operation that is subsequent to the first imaging operation.

16. The imaging apparatus according to claim 1, wherein the imaging unit is above the irradiation unit so as to overlap with the irradiation unit.

17. The imaging apparatus according to claim 1, further comprising an authentication unit configured to authenticate a user based on a combined image.

18. The imaging apparatus according to claim 17, wherein the authentication unit is further configured to authenticate the user based on feature information of a fingerprint appearing on a fingertip of the user.

19. An imaging method, comprising:
in an imaging apparatus including an irradiation unit that irradiates a subject with light, an imaging unit that images the subject a plurality of times to obtain a plurality of imaged images, a central processing unit (CPU) that controls the imaging unit and the irradiation unit, and combines the plurality of imaged images, the imaging unit having a plurality of imaging elements disposed in a matrix, the irradiation unit having a plurality of light emitting elements, wherein each light emitting element of the plurality of light emitting elements is associated with a corresponding imaging element of the plurality of imaging elements:
turning on a first set of light emitting elements of the plurality of light emitting elements;
turning off a second set of light emitting elements of the plurality of light emitting elements, wherein the second set of light emitting elements is different from the first set of light emitting elements; and
driving a set of imaging elements of the plurality of imaging elements, wherein the set of imaging elements is associated with second set of light emitting elements.

20. A non-transitory computer-readable medium having stored thereon, computer-executable instructions which, when executed by a central processing unit (CPU) of an imaging apparatus including an irradiation unit that irradiates a subject with light, an imaging unit that images the subject a plurality of times to obtain a plurality of imaged images, the CPU that controls the imaging unit and the irradiation unit, and a combination unit that combines the plurality of imaged images, the imaging unit having a plurality of imaging elements disposed in a matrix, the irradiation unit having a plurality of light emitting elements, wherein each light emitting element of the plurality of light emitting elements is associated with a corresponding imaging element of the plurality of imaging elements, causes the CPU to execute operations, the operations comprising:
turning on a first set of light emitting elements of the plurality of light emitting elements;
turning off a second set of light emitting elements of the plurality of light emitting elements, wherein the second set of light emitting elements is different from the first set of light emitting elements; and
of driving a set of imaging elements of the plurality of imaging elements, wherein the set of imaging elements is associated with the second set of light emitting elements.

* * * * *